United States Patent
Schrezenmeir

(10) Patent No.: US 9,644,210 B2
(45) Date of Patent: May 9, 2017

(54) PROBIOTIC GRAM-POSITIVE BACTERIA FOR THE PROPHYLAXIS, SUPPRESSION, OR ELIMINATION OF ALLERGIC REACTIONS IN HUMAN

(71) Applicant: Jürgen Schrezenmeir, Karlsruhe (DE)

(72) Inventor: Jürgen Schrezenmeir, Karlsruhe (DE)

(*) Notice: Subject to any disclaimer, the term of this patent is extended or adjusted under 35 U.S.C. 154(b) by 0 days.

(21) Appl. No.: 14/089,502

(22) Filed: Nov. 25, 2013

(65) Prior Publication Data
US 2014/0288159 A1    Sep. 25, 2014

Related U.S. Application Data

(63) Continuation-in-part of application No. 12/528,124, filed as application No. PCT/DE2007/000333 on Feb. 22, 2007, now abandoned.

(51) Int. Cl.
| | | |
|---|---|---|
| *A61K 35/74* | (2015.01) | |
| *C12N 15/11* | (2006.01) | |
| *C12N 15/117* | (2010.01) | |
| *A61K 35/741* | (2015.01) | |

(52) U.S. Cl.
CPC .......... *C12N 15/117* (2013.01); *A61K 35/741* (2013.01); *C12N 2310/17* (2013.01)

(58) Field of Classification Search
None
See application file for complete search history.

(56) References Cited

U.S. PATENT DOCUMENTS

2011/0020283 A1*  1/2011  Schrezenmeir ...... A61K 35/745
                                                                                         424/93.3

OTHER PUBLICATIONS

De Vrese "Effect of Lactobacillus gasseri PA 1/8, Bifidobacterium longum SP 0/3, B. bifidum MF 20/5 on common cold episodes: A double blind randomized, controlled trial", Clinical Nutrition, (2005) 24, 481-491.*
"Final Report of the Governmental Authority BgVV" (German language), Published Oct. 1999.

* cited by examiner

*Primary Examiner* — Robert Yamasaki
*Assistant Examiner* — Charles Zoltan Constantine
(74) *Attorney, Agent, or Firm* — Edwin D. Schindler

(57) ABSTRACT

A method for a prophylaxis, suppression or elimination of an allergic reaction in a human, or for shifting the TH1-TH2 balance in a human body toward an increase of TH1 or a decrease of TH2 or both an increase in TH1 and a decrease in TH2, includes the steps of preparing a pharmaceutical composition having genomic DNA of at least one probiotic, gram-positive bacteria strain selected from the group *Lactobacillus gasseri* PA 16/8, *Bifidobacterium bifidum* MF 20/5, *Bifidobacterium bifidum* MG 20/5, *Bifidumbacterium longum* SP 07/3, *Lactobacillus rhamnosus* GG (92164) or a combination thereof, as an active ingredient, the at least one probiotic, gram-positive bacteria strain being present in the form of at least one of viable bacteria and inactivated bacteria, and administering to a human as suppository, vaginally, as a cream applied to skin, rectally, as a subcutaneous injection, as intravenous injection, as an inhalation liquid, or orally in combination with food.

2 Claims, 40 Drawing Sheets

Figure 1:
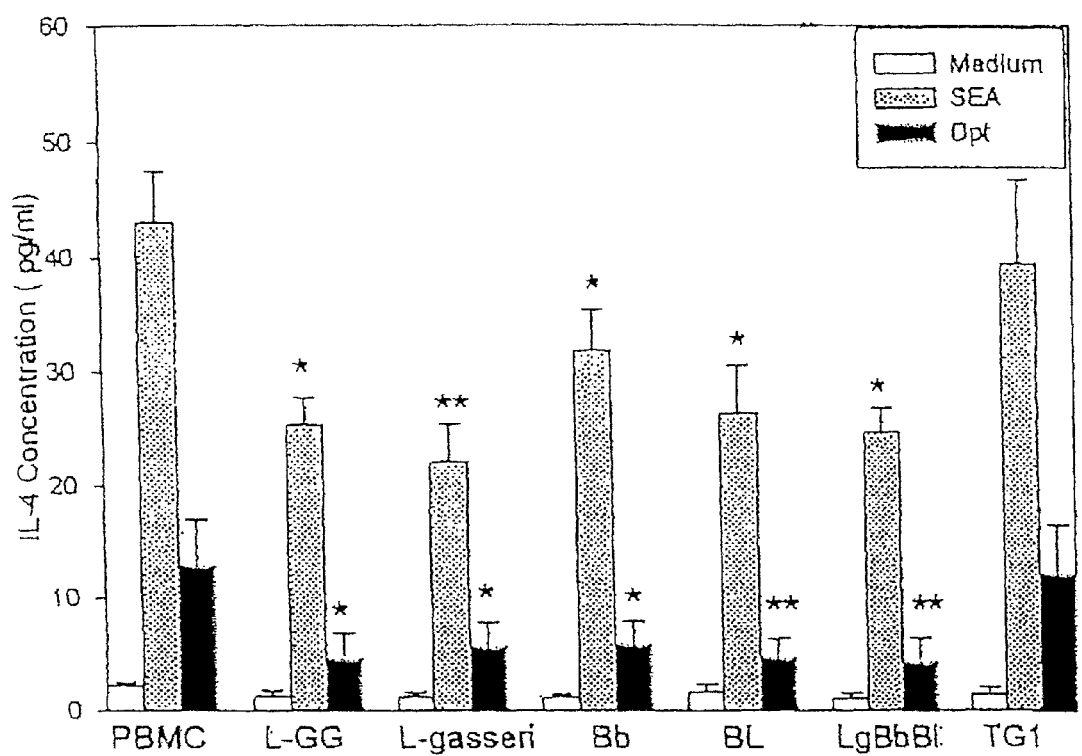
Figure 1:
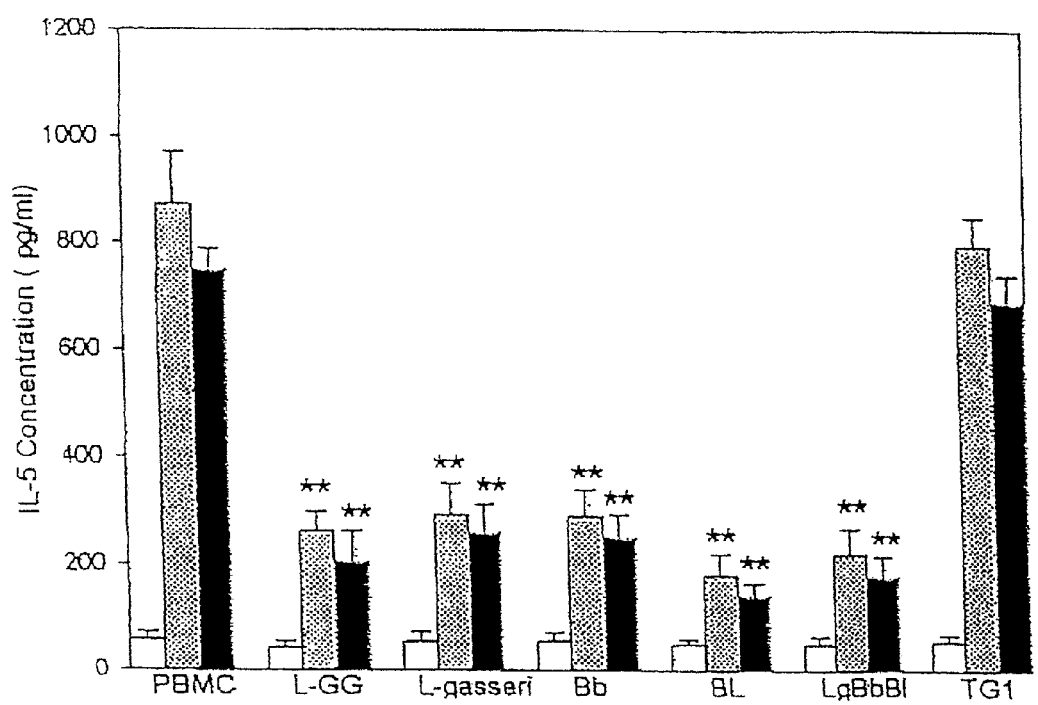
Figure 1:
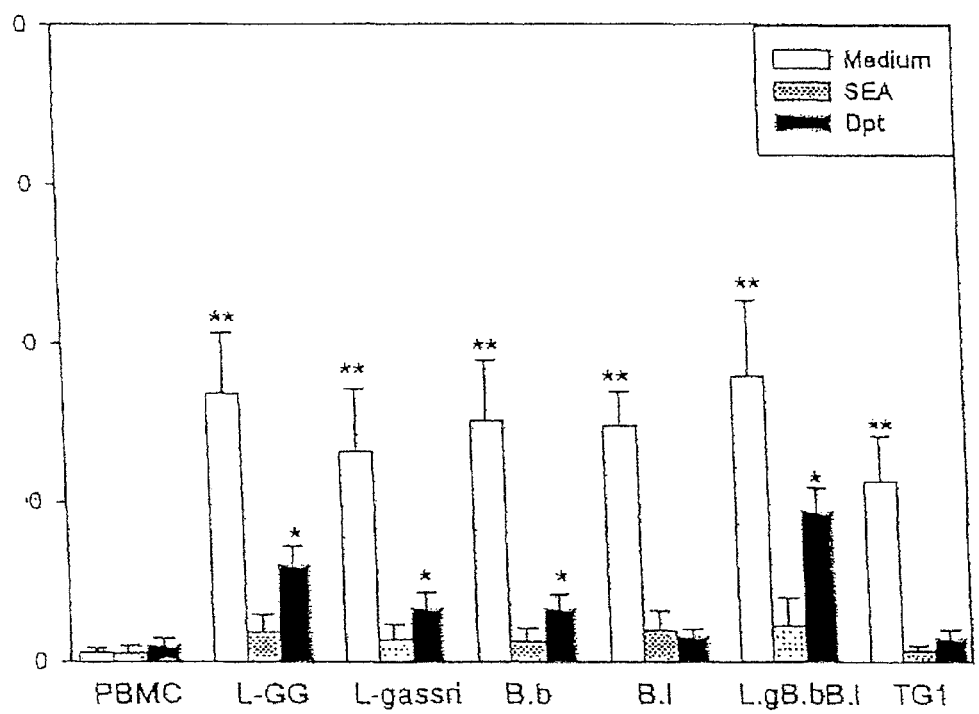
Figure 1:
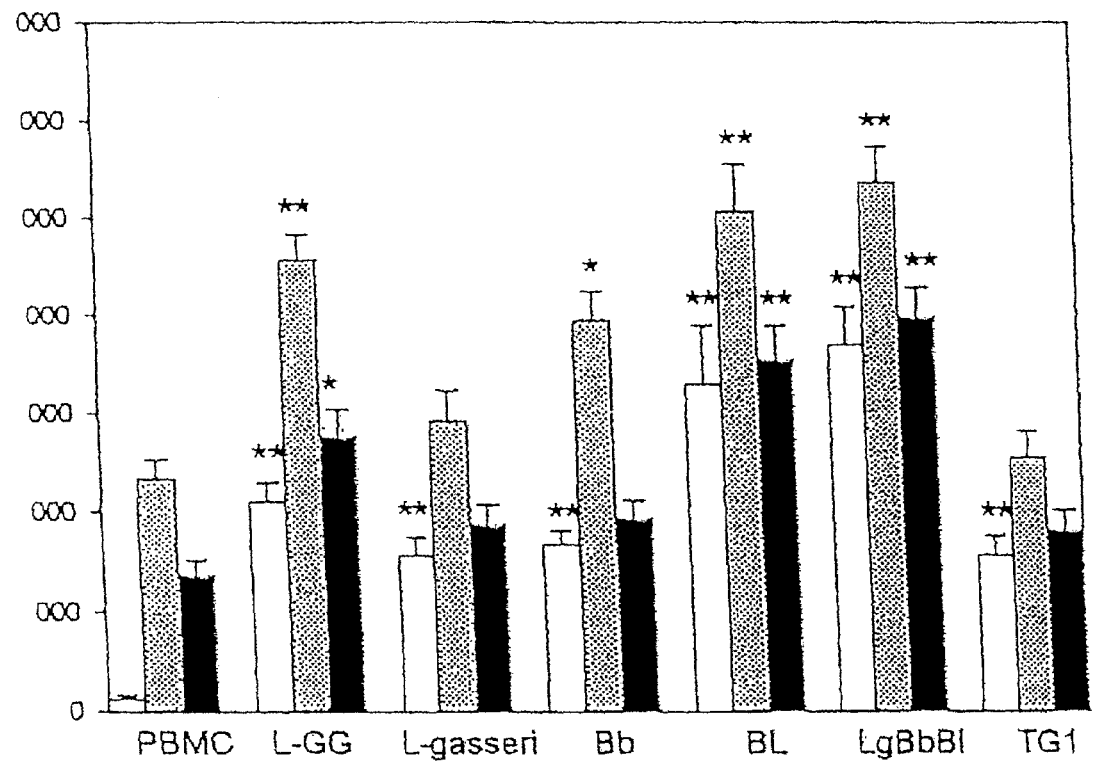
Figure 1:
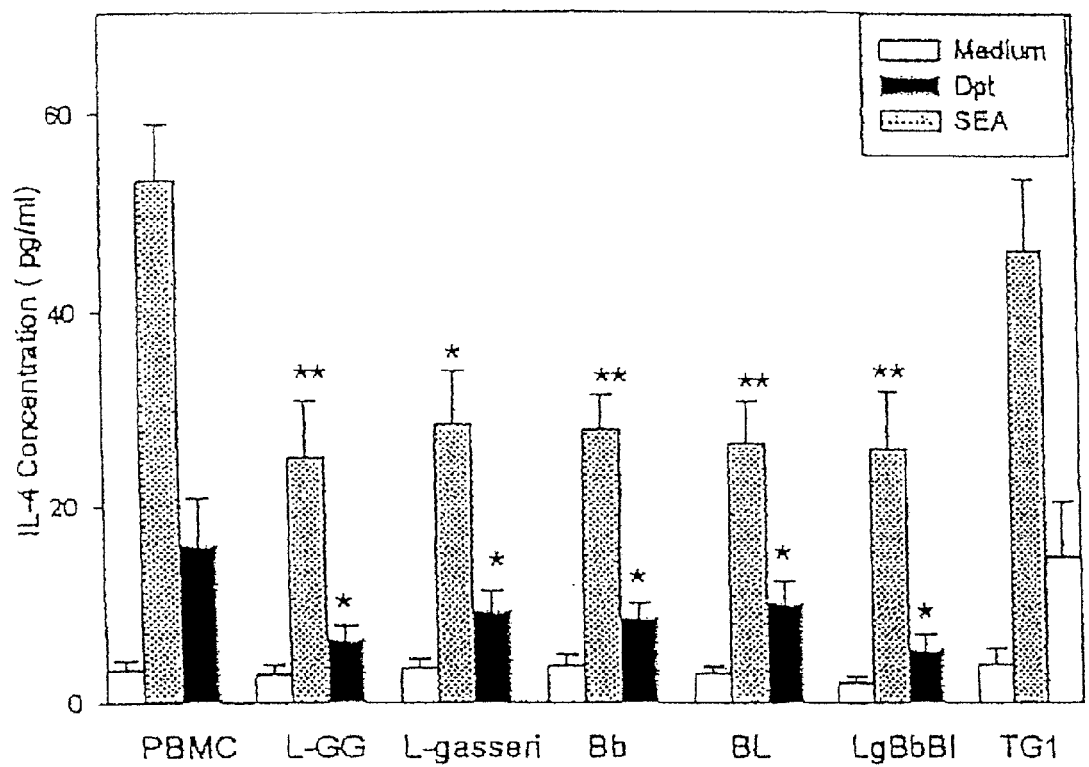
Figure 1:
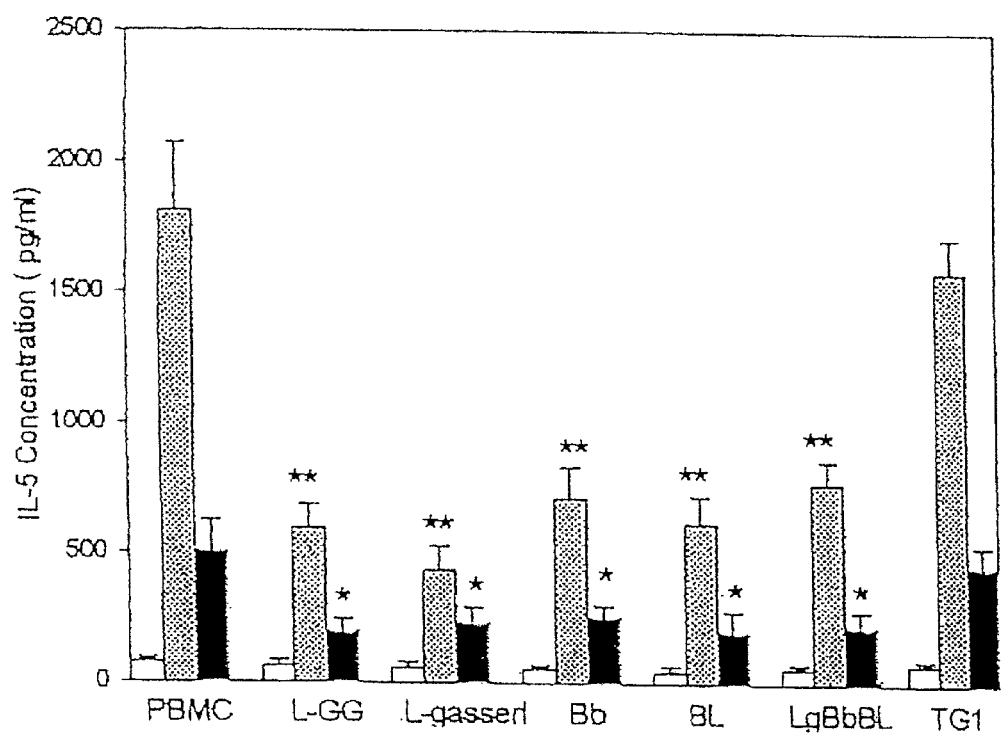
Figure 1:
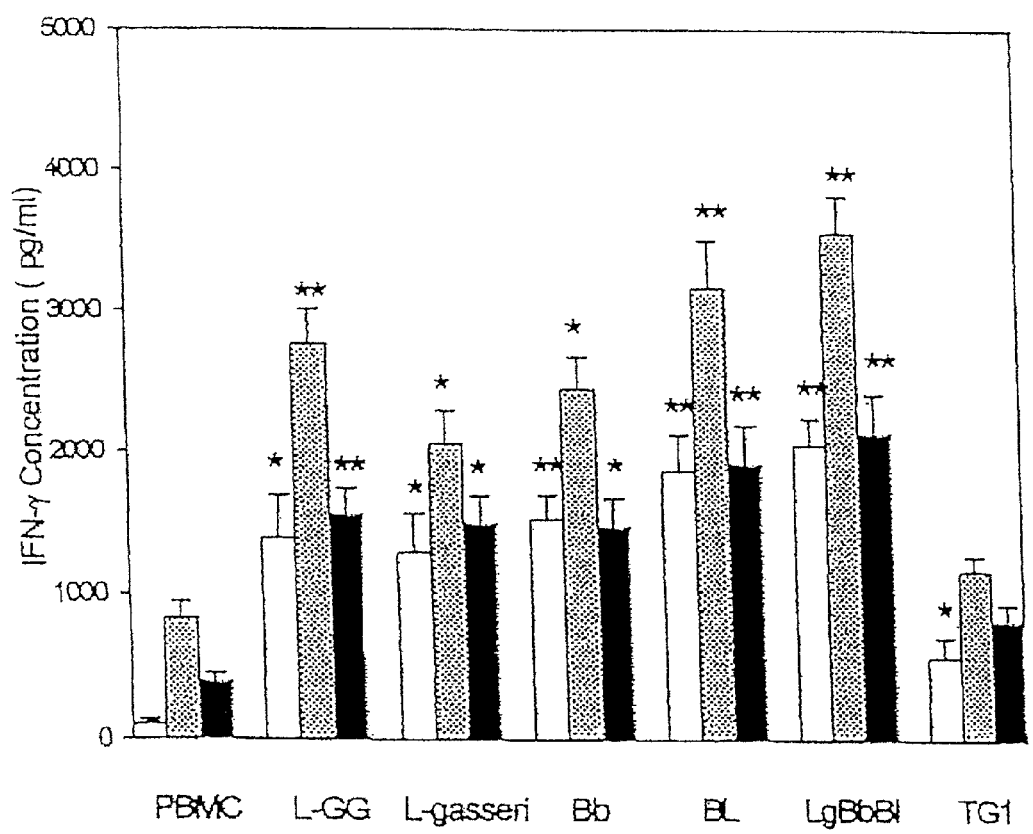
Figure 1:
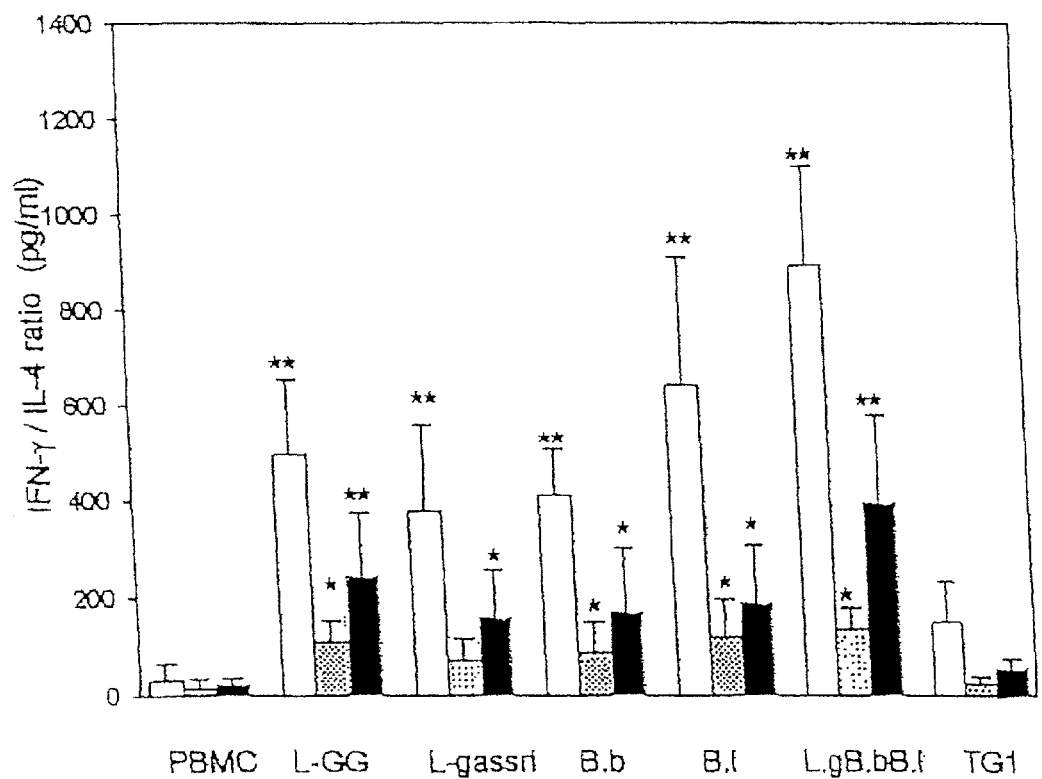

PROBIOTIC GRAM-POSITIVE BACTERIA FOR THE PROPHYLAXIS, SUPPRESSION, OR ELIMINATION OF ALLERGIC REACTIONS IN HUMAN

CROSS-REFERENCE TO PRIOR APPLICATION

This is a continuation-in-part of U.S. patent application Ser. No. 12/528,124, filed Oct. 11, 2010, now abandoned, which represents the U.S. National Phase application of P.C.T. Application No. PCT/DE2007/000333, filed Feb. 22, 2007, the entire disclosure of which shall be deemed to be incorporated by reference herein.

BACKGROUND OF THE INVENTION

Technical Field of the Invention

The present invention relates to a pharmaceutical and related method for its application for the prophylaxis, suppression, or elimination of allergic reactions in humans.

More particularly, the present invention pertains to a pharmaceutical and its method for application for the treatment of allergic reactions commonly experienced by pregnant females and females or infants after birth with the goal of reducing allergies, such as, for example, atopic dermatitis and allergic rhinitis, infections and metabolic disorders due to inflammation in the infant later in life.

Description of the Prior Art

Allergic reactions to substances such as pollens (hay fever) or other components of plants, cat fur and other animal hairs, dust including the house dust mite droppings it contains, insect poison, foods such as milk or nuts, or perfumes and other components of cosmetics are well known and a growing problem for increasing numbers of people.

The cause of this is that the body's own immune system reacts to such substances as though they are actually harmful invaders, such as parasites. Moreover, the extent of the reaction is excessive.

In the course of this autoimmune response, the white blood corpuscles, the lymphocytes, play a considerable role. One form of lymphocytes are the T lymphocytes, or helper cells (TH cells), which secrete various mediators, cytokines, for controlling the immune responses. There are—firstly—cytokines that reduce or prevent the allergic reactions and—secondly—other cytokines that trigger inflammatory, that is to say allergic, reactions by having a stimulating effect as moderators on actor cells such as mast cells. According to this effect, all TH cells are classified into two groups, namely $T_H1$ and $T_H2$ cells. $T_H1$ cells comprise antiallergic cytokines, such as γ-interferon (IFN-γ) or interleukin-2 (IL-2). $T_H2$ cells comprise mediators that trigger allergic reactions, such as interleukins IL-3, IL-4, IL-5 and IL-10. Interleukin-4 stimulates the mast cells to form the antibody immunoglobulin type E (IgE), which is present in very large amounts in allergies.

The ratio between the number of $T_H1$ cells and $T_H2$ cells is crucial for the body's immune response to invaded pathogens. It is significantly lower in patients with an allergic reaction than in healthy people. It is known that newborn or premature babies also have a very low value so that the mother organism does not mistakenly attack the infant's cells.

The $T_H1$-$T_H2$ balance is therefore an important characteristic of each human and is also increasingly well known to a wider public.

It is generally supposed that changes to the intestinal flora and/or the lack of bacterial stimulation in very early childhood, as a result of excessive hygiene and a decrease in infectious diseases, creates the predisposition for a divergence of the value of the balance, and therefore gives rise to allergic oversensitivity.

Even in infancy, therefore, the invasion of allergens can cause inflammatory reactions, such as running noses and swollen mucosae, and even increased body temperature.

Numerous pharmaceuticals are known that combat or suppress the occurring symptoms. They have the disadvantage that they are often very expensive, trigger a number of undesirable side effects and must be continually taken by the patient.

SUMMARY OF THE INVENTION

Against this background, it is the object of the invention to identify an active substance that is already known and can be produced on an industrial scale, is therefore readily available and processable, which generates low costs, which already occurs in marginal amounts even in the ambit of healthy persons, and is therefore compatible with the human organism in certain limits, and which does not attack the allergic reactions at the level of the symptoms but at the stage of triggering by mediators.

To achieve this object, the invention proposes a pharmaceutical and a method for its application in which probiotic, gram-positive bacteria, such as *Lactobacillus* and *Bifidobacterium* are present as as the substantial active ingredient, specifically as viable bacteria and/or inactivated bacteria and/or the genomic DNA thereof.

The pharmaceutical or food supplement composition of the present invention is preferably and beneficially a prophylaxis, suppression or elimination of an allergic reaction in a human, or for shifting the TH1-TH2 balance in the human body toward an increase of TH1 or a decrease of TH2, or both, an increase in TH1 and a decrease in TH2.

The preferred bacterial strains that should be incorporated within the pharmaceutical composition and applied via a method in accordance with the claimed invention include *Lactobacillus* gasseri (PA 16/8), *Bifidobacterium bifidum* (MF 20/5), *Bifidobacterium bifidum* (MG 20/5), *Bifidobacterium longum* (SP 07/3) and LgsB.bB.I, and a mixture of one or more of *Lactobacillus gasseri*, *Bifidobacterium bifidum* and *Bifidobacterium longum*. All of the foregoing bacterial strains have been deposited at the National Institute of Technology and Evaluation ("NITE") Patent Microorganisms Depositary, 2-5-8 Kazusakamatari, Kisarazu-shi, Chiba-ken 292-0818, Japan and is an International Depositary Authority under the Budapest Convention. The culture collection number accorded *Lactobacillus gasseri* PA 16/8 is NITE BP-819; the culture collection number accorded *Bifidobacterium bifidum* (MF 20/5) is NITE BP-817; and the culture collection number accorded *Bifidobacterium longum* SP 07/3 is NITE BP-818. The foregoing biological deposits were made no later than 2012.

The inventor has deposited the bacterial strains required for practicing the present invention, as required under the Budapest Treaty on the International Recognition of the Deposit of Microorganisms, which deposit has been accepted, and that all restrictions on the availability to the public of the deposited material so deposited are irrevocably removed no later than the date of issuance of the United States patent.

The pharmaceutical composition of the present invention may be provided to pregnant women and women and/or infants after birth with the goal of reducing allergies, such as, for example, atopic dermatitis and allergic rhinitis, infections and metabolic disorders due to inflammation in the infant and later in the life of the infant.

Preferred applications of the pharmaceutical composition of the present invention may include oral administration, application to the skin or to the mouth of, for example, the infant with a liquid or a cream containing the referenced strains and/or vaginal or rectal application before or after birth to the pregnant women, e.g., by a suppository or a tampon.

In the case of allergic dermatitis, cream may be used for applying the strains to the affected parts of the person's skin, whether it be for application by the pregnant woman or her infant.

In cases of allergic rhinitis, application may be accomplished via a cream or a powder, which is applied after dispersion of the strains in a solution preferably containing glucose or similar sugars as nutrients and for providing isoosmolar milieu.

The attribute "probiotic" is explained in Brockhaus as the coexistence of two organisms for the benefit of one partner without damaging the other. In the case of this invention, a second organism, namely the bacterium, is of use to the human organism. The bacterium itself is not harmed, and therefore remains viable. That includes that fact that, with oral administration, as many bacteria as possible pass unharmed through the stomach with its acids, enzymes and other digestive agents.

The term "probiotic" also implies that disadvantageous effects on the human are negligible or at least very small, and that effects predominantly occur that are classified as useful.

The term "probiotics" means preparations of microorganisms that have a health-promoting effect on the host organism when consumed in sufficient amounts. Probiotic lactic acid bacteria (*Lactobacillus*) have been used for the longest time. Probiotics can be administered as specially prepared foods or in the form of pharmaceuticals.

The health-promoting effects of probiotics are strain-specific in each case. Probiotic bacterial strains are known that, according to evidence-based medicine, demonstrably promote lactose digestion, suppress pathogenic microorganisms in the intestine and limit or suppress diarrhea.

Other bacterial strains increase protection against infection, lower the cholesterol level and reduce the risk of colon cancer.

These effects have been successfully demonstrated in vitro before their widespread application. It is therefore legitimate to validate the health-promoting effect of this invention with a series of laboratory experiments.

By means of the experiments described below, it was measured which cytokines from a fraction of human blood cells (PBMC—peripheral blood mononuclear cells), are released under particular conditions. For one series of experiments, these blood cells were isolated from the blood of healthy humans and for a second series of experiments from the blood of allergic patients who were allergic to house dust.

For stimulation, staphylococcal enterotoxin type A (SEA) and in a further series *Dermatophagoides* (Dpt) were added because housedust allergy sufferers are usually also allergic to these. The invasion of an allergenic substance is thereby simulated.

The γ-interferon was measured as a surrogate for the $T_H1$ reaction. The $T_H2$ pattern was recorded by means of the secreted interleukins 4 and 5 (IL-4 and IL-5).

The factors that may be involved in the increased spread of allergic disease are thought to include the modification of intestinal flora or the lack of bacterial stimulation during childhood. $T_H2$ cytokines increase the production of IgE and stimulate mast cells. On the other hand, γ-interferon (IFN-γ), a $T_H1$-cytokine, contributes to suppressing IgE synthesis. In this manner, the imbalance in the "$T_H1$ to $T_H2$" expression can contribute to triggering and maintaining allergic diseases. *Lactobacillus* bacteria, which form part of the natural microflora inside the intestine are supposed to reduce the frequency and severity of allergic manifestations and modulate the $T_H1/T_H2$ response. The functional mechanism has still not been elucidated.

Goal: Our experimental goal was to determine the influence of probiotic bacteria on the production of type $T_H1$ and $T_H2$ cytokines of healthy humans and patients with house dust mite allergies and explain the molecular basis of the effects of bacterial genomic DNA on the $T_H1/T_H2$ response to staphylococcal enterotoxin A (SEA) and *Dermatophagoides pteronyssinus* (Dpt) and compare them with the effects of living bacteria. Methods: PBMCs from patients with allergies to house dust mites in comparison to those from healthy donors were incubated for 24 and 48 hours with or without SEA and Dpt allergens. The effect of preincubation with living probiotic bacteria, as well as the influence of their genomic DNA, which was simultaneously added to the cultured and incubated for 24 hours, was assessed by measurement of the $T_H1/T_H2$ cytokine production.

Results

The tested, viable, gram-positive, probiotic bacteria and their genomic DNA showed that they suppressed SEA and Dpt-stimulated secretion of $T_H2$ cytokines (EL4 and EL5) and extended the stimulation of IFN-γ. This effect depended both on the dosage and on the chosen bacterial strain. No significant inhibition was triggered by the control gram-negative *Escherichia coli* TG1. Probiotic bacteria reduced the production of IL-4 cytokines from allergic PBMCs, particularly after restimulation with SEA and Dpt, even more effectively than in healthy humans. On the other hand, IL-5 inhibition in healthy subjects was more clearly pronounced. Bacterial DNA also suppressed the release of IL-4 and IL-5, but only to a somewhat lower extent. The inhibition of EL4 was more pronounced in the case of PBMCs from allergic subjects than for healthy subjects, although this was the case for EL5.

SUMMARY

The $T_H1/T_H2$ response to allergens, modulated by the tested probiotic bacteria, as well as their genomic DNA, showed an anti-$T_H2$ activity. Consequently various strains of probiotic bacteria and their genomic DNA can be useful in preventing allergic diseases.

DETAILED DESCRIPTION OF THE INVENTION

1. Introduction

The teaching of the causes of allergic diseases remains unclear, though human experimental studies show that genetic conditions contribute to the immune response of the intestinal mucosa and enteritic bacteria contribute to the pathogenesis of allergic diseases. Some studies propose that $T_H2$ cytokines, particularly IL-4, IL-5, IL-9 and IL-13, play essential roles in the pathogenesis by regulating the production of IgE and stimulating mast cells. The production of IL-4, IL-5, IL-9 or IL-13 by $T_H2$ lymphocytes at a high level can play a decisive role in the development and progress of allergic responses; by contrast, IFN-γ, a so-called $T_H1$ cytokine, has the capability to suppress IgE synthesis. Defective IFN-γ expressions are often linked to IgE-mediated allergies. The dysregulation in the balance of $T_H1/T_H2$ cytokines can to a large extent be made responsible for triggering and maintaining allergic inflammation processes in illnesses such as bronchial asthma or atopic dermatitis.

It has been proposed that, particularly, the $T_H2$ cytokine profile of newborn babies; ageing, which normally reduces the $T_H1/T_H2$ balance; modern hygiene regulations; intensive sterilization of food and/or changes in the intestinal flora of newborn babies caused by feeding an artificial formulation play major roles in the changes in the $T_H1/T_H2$ balance. The acquired knowledge in this field has prepared the ground for a number of new therapies. One approach is simply to use probiotic bacteria to reproduce those cytokines that have not been formed in sufficient amounts or to reduce those cytokines that have been formed on too large a scale because probiotic bacteria modulate the $T_H1/T_H2$ balance.

Probiotic bacteria are generally classified as safe and have been consumed by humans or animals. The bacteria *Lactobacillus* and *Bifiobacterium* are the microorganisms most widespread in the human gastrointestinal tract. Interest is growing in the immune-stimulating effect of probiotic bacteria, in particular their antiallergenic effect. The important role of bacteria in allergic diseases raises the possibility of preventing or treating these deviations by modifying the intestinal microflora by probiotic treatment. The probiotic bacteria can act directly or indirectly by modulation of the endogenous flora or of the immune system. It was proposed to use the new expression "immunobiotics" for bacteria that promote health via the mucosal immune system, in contrast to those with only a local effect. Various immune responses to probiotics have been reported, such as the secretion of inflammation-promoting cytokines, the reproduction of lymphocytes and the formation of nitrogen oxides. Furthermore, it has been shown that entire cells, some soluble components that were secreted by LGG or the DNA from LGG, components of the cell wall such as peptidoglycan or lipoteichionic acids of Lactobacilli trigger inflammatory immune responses and immunobiotic activities. It was demonstrated that not only living bacteria, which are administered in the intestinal tract, but also isolated probiotic DNA is active, even if it is injected subcutaneously.

It has been reported that undenatured CpG motifs in bacterial DNA are mitogenic for B-cells of mice and trigger the production of inflammatory cytokines by macrophages and dendritic cells (DC). And CpG oligodeoxynucleotides (ODNs) and bacterial DNA trigger the production of interleukin 6 (IL-6), interleukin 12 (IL-12) and interferon-γ (IFN-γ) by B-lymphocytes and natural killer cells of mice. Moreover, the CpG DNA induces the propagation of B-cells and the division of uninfluenced and activated T-cells in T-helper cells 1 and 2. Specific CpG ODNs (D-type) are particularly efficient at activating NK cells and the production of α-interferon (IFN-α) by plasmacytoid dendritic cells, while other ODNs (K type) are particularly effective activators of B cells. It was recently found that the toll-like receptor 9 (TLR9) plays a critical role in triggering cellular activation by CpG DNA.

Experiments that are performed in mice that have been sensitized to ovalbumin showed that, after administration of lactic acid bacteria in the stomach, the particular IgE and $T_H2$ profile-dependent, inflammatory responses were suppressed. Furthermore, the latest reports propose that the *Lactobacillus rhamnosus* GG can reduce the symptoms of allergic diseases in human subjects, in a similar way to how it can trigger congenital immune responses by activating transcription factors, which are integrated into the signalling function of cytokines. The administration of this bacterial strain to nursing mothers and newborn babies led to suppression of the risk of atopic eczema in babies. In-vitro experiments have shown that the stimulation of PBMCs or monocytes of healthy donors by a variety of lactic acid bacteria induces the secretion of IL-12, which is an essential pro-$T_H1$ cytokine and is involved in the control of the development of allergic diseases. The functional mechanisms by which the LAB influences the production of $T_H2$ cytokines, which are responsible for initiating the development of allergic diseases, remain to be identified. Taking into account the presence of undenatured DNA sequences (CpG motifs) in the chromosomes of the DNA from *Bifidobacterium* and *Lactobacillus*, we decided in this study to examine the effect of four strains of the bacteria *Lactobacillus* and *Bifidobacterium*, as well as their chromosomal DNA on IL-4, IL-5 and IFN-γ production by SEA- and Dpt-stimulated PBMCs of healthy and allergic test subjects. The bacteria *Lactobacillus* and *Bifiobacterium* investigated showed anti-$T_H2$ activities and the pro-$T_H1$ cytokine, IFN-γ.

2. Methods and Material

2.1. Bacterial Culture

In this study, the following bacterial strains were used: *Lactobacillus rhamnosus* GG (92164), *Lactobacillus gasseri* (PA 16/8), *Bifidobacterium bifidum* (MF 20/5), *Bifidobacterium bifidum* (MG 20/5), *Bifidobacterium longum* (SP 07/3) and LgsB.bB.I (a mixture of *Lactobacillus gasseri, Bifidobacterium bifidum* and *Bifidobacterium longum*). *Bifidobacterium* and *Lactobacillus* strains were used (a 0.02% inoculum of strains that had been anaerobically stored at minus 80° C. in 30% glycerol) (anaerobic system, MACS-VA500 Workstation with airlock and airlock, Don Whitley Scientific Limited UK in an MRS medium (MRS; Merck, Darmstadt, Germany), supplemented with 0.05% L-cystein at 37° C. for 16 hours. Before harvesting and washing in PBS, consecutive solutions of freshly prepared cultures were applied to plates containing MRS-agar media and cultivated for counting. The count of the colony-forming units (CFU $ml^{-1}$) of the probiotic bacteria groups was derived by applying repeated 10-fold solutions to the plates. The plates were anaerobically incubated at 37° C. for 24-48 hours. The bacteria were then washed three times with PBS and adjusted to the final concentrations of $10^{10}$, $10^7$ and $10^1$ CFU $ml^{-1}$. The bacterial suspension was stored at −80° C. in an MRS solution containing 30% glycerol. For all bacterial strains, normal growth curves were prepared by recording OD600 vs agar plate counts of freshly prepared, repeatedly dissolved cultures. To calculate the counts of viable bacteria in freshly prepared cultures, the curves were fitted with logarithmic printouts that obtained all values over 98.5% (data not shown). Gram-negative *E. coli* TG1 (product number BU-00035) was purchased from Maxim Biothec Inc. and grew in LB-medium for 18 hours at 37° C. and was harvested as above.

2.2. Preparation of Genomic DNA from Bacteria

Genomic DNA from pure cultures of probiotic bacteria was purified by extraction with phenol/chloroform/isoamyl alcohol (25:24:1). To obtain complete cell disruption, the method was slightly modified by extending the enzymatic lysis from 2 to 7 hours. Subsequently the DNA was precipitated, sterilized with cold (−20° C.) 95% ethanol and dissolved in double-distilled water (ddH$_2$O). The concentration and purity of all DNA preparations were derived by measuring the OD$_{260}$ absorption or the OD$_{260/280}$ and OD$_{260/230}$ ratios. Only DNAs with an OD$_{260/280}$ ratio>1.8 and OD$_{260/230}$>2 were used. DNAs were purified from endotoxin with TritonX-114D and also investigated for their content of lipopolysaccharides (LPS) using the limulus amaebocytes test (QCL-1000, CAMBREX, Germany). The LPS content was less than 0.01 U endotoxin $\mu g^{-1}$.

To determine a bioactivity of LPS or other bacterial contaminants in the DNA preparations, the DNA was degraded with DNase I (Sigma). There was no demonstrable suppression of cytokines by PBMCs below the base level when the degraded DNA with a concentration of 75 $\mu ml^{-1}$ was added (measured before the DANN disruption treatment).

2.3. PBMC Isolation and Culture 2.3.1. Preincubation of PBMCs with Probiotic Bacteria and Further Stimulation with SEA and Dpt Eight allergic patients and eight healthy donors were recruited for the study. All test subjects submitted verbal and written agreement before registering for this study, as required by the ethics commission of the University of Kiel on the use of human test subjects in research. Venous blood was directed from the donors into heparinized Vacutainers and diluted 1:1 with 0.9% NaCl. Then fresh peripheral blood mononuclear cells (PBMCs) from heparinized dilute blood were isolated by centrifuging according to increasing density (1.077 g ml$^{-1}$) (Lymphoprep, AXIS-SHIELD PoC AS, Oslo, Norway). The cells were emulsified in RPMI-1640 culture medium (Sigma, Munich, Germany), supplemented with 10% (v/v) heat-activated (56° C., 1 hour) foetal bovine serum, Gentamicin (50 $\mu g$ ml$^{-1}$) (Sigma), penicillin streptomycin (1%) and sodium pyruvate solution (0.23 mmol l$^{-1}$) (Sigma) (ordered as complete medium). All components were purchased endotoxin-tested, as required by the LAL. The cells were cultivated in complete medium in a concentration of 2*10$^6$ cells ml$^{-1}$ in vessels with 24 wells. At the same time, for stimulation, four strains of living probiotic bacteria and a gram negative bacterium (E. coli TG1) were added to the cultures. As required for bacterial counts, the probiotic and the other bacteria were viable at the time of addition to the cultures. The cells that were cultivated only with the medium served as a non-stimulated control. The tests for dependency on the dosage, performed for IL-4 and IL-5 as cultures with an ultimate volume of 200 $\mu$l/well were prepared in flat-bottomed 96-well microtitre plates (Nune, Roskilde, Denmark) with 2×10$^6$ mononuclear cells and 5×10$^4$, 5×10$^5$, 2×10$^6$, 5×10$^6$, 2×10$^7$, and 5×10$^7$ bacteria/ml corresponding to 0.025, 0.25, 1, 2, 5, 10 and 25 bacteria per mononuclear cell. They indicated that the maximum suppression with 2×10$^7$ CFU bacteria/ml, corresponding to a ratio of 10:1 (bacteria to PBMC) was observed. This concentration was used in other experiments. The ultimate ratio between PBMC and bacteria (ratio of bacteria to PMBC) was 10:1 for healthy donors and for allergic patients. For control treatment, only culture medium was added to the PBMC solution. Then, and after three hours incubation at 37° C., the PBMCs were further stimulated with SEA (2 $\mu g$ ml$^{-1}$) or Dpt (2000SQ-E ml$^{-1}$ equivalent to 2 $\mu g$ dose ml$^{-1}$) and in a 5% CO$_2$-moistened incubator at 37° C. for 48 hours.

All experiments were performed in duplicate. After incubation for 48 hours, the culture medium was centrifuged at 4° C. for 20 minutes at 1,000×g. The cell-free supernatant was sterilized by passing through a filter with a pore size of 0.2 $\mu$m (Millipore, Germany) and stored at −80° C. until use. The viability of the cells was determined before and after incubation with bacteria by exclusion with trypan blue.

2.3.2. Stimulation with SEA, LPS and Genomic DNA

Fresh PBMC from heparinized peripheral blood from four healthy donors was isolated by centrifuging according to increasing density (1.077 g ml$^{-1}$) (Lymphoprep, AXIS-SHIELD PoC AS, Oslo, Norway). The cells were emulsified in RPMI 1640 culture medium (Sigma, Munich, Germany), supplemented with 10% (v/v) heat-activated (56° C., 1 hour) foetal bovine serum, Gentamicin (50 $\mu g$ ml$^{-1}$) (Sigma), penicillin streptomycin (1%) and sodium pyruvate solution (0.23 mmol l$^{-1}$) (Sigma) (complete medium). All components were purchased endotoxin-tested. All tests for dependency on the dosage, performed for IL-4 and IL-5 as cultures with an ultimate volume of 200 $\mu$l/well were prepared in flat-bottomed 96-well microtitre plates (Nune, Roskilde, Denmark) with 2×10$^6$ mononuclear cells and 5, 10, 25, 50, 75 and 100 $\mu g$ genomic DNA per ml. They indicated that the maximum suppression with 75 $\mu g$ DNA ml$^{-1}$ could be observed. This concentration was used in the further experiment. The cells were cultivated in a complete medium in a concentration of 2*10$^6$ cells ml$^{-1}$ in a 24-well plate (Nune, Roskilde, Denmark). At the same time genomic DNA (75 $\mu g$ ml$^{-1}$) of probiotic bacteria, genomic DNA from calf (75 $\mu g$ ml$^{-1}$ Sigma, Munich, Germany) SEA (2 $\mu g$ ml$^{-1}$) and LPS from E. coli (20 $\mu g$ ml$^{-1}$, Sigma, Munich, Germany) were added to the culture and incubated at 37° C., 5% CO$_2$-moistening for 24 hours. All experiments were performed in triplicate. After 24 hours' incubation, the cell-free supernatants were collected and centrifuged for 1000×g for 20 minutes at 4° C., and sterilized by passing through a filter with 0.2 $\mu$m pores (Millipore, Germany) and stored at −80° C. in aliquots until analysis. The viability of the cells was determined before and after incubation with genomic DNA by exclusion with trypan blue. In all experiments 95 to 98% of the PBMCs were viable. The experiments for dependency on the dosage, which was performed for all cytokines indicated that the maximum suppression is observed at a concentration of 75 $\mu g$ ml$^{-1}$. This concentration was used in the further experiments.

2.4. Investigation of the Cytokines by Means of Enzyme-Linked Immunosorbent Analysis (ELISA)

The concentration of IL-4, IL-5 and IFN-$\gamma$ was quantified in the cell-free supernatants by means of a special ELISA (BD OptEiA™ set human IL-4, 5 and IFN-$\gamma$, Heidelberg, Germany). The detection limits of investigation was 0.5 $\mu g$ ml$^{-1}$ for IL-4, 0.5 $\mu g$ ml$^{-1}$ for IL-5 and 1 $\mu g$ ml$^{-1}$ for IFN-$\gamma$. The optical density values of the samples were read at 450 and 570 nm on an ELISA plate reader. The experiments were repeated at least twice and performed in triplicate.

2.5. Statistical Analyses

The experimental data of the test were output by means of ±S.E.M and a non-parameterized, statistical analysis with the t-test was performed. P values of less than 0.05 were considered statistically significant.

Results

*Lactobacillus* and *Bifidobacterium* suppress IL-4 and IL-5 and trigger IFN-γ production by SEA or Dpt-stimulated PBMCs from healthy donors. It was shown that streptococcal superantigenes trigger a high concentration of IL-4 and IL-5 from PBMCs from healthy donors and the heat-killed lactic acid bacteria were capable of suppressing the secretion of a type-2 cytokine profile. Furthermore, a study has shown that allergic patients had an increased content of IL-4 and IL-5. *Dermatophagoides pteronyssinus*, Dpt (at 83.8%) and *Dermatophagoides farinae*, Df (at 78.4%) are the most widespread causative allergens in patients with allergic rhinitis. Now we have confirmed these observations with another superantigen: staphylococcal enterotoxin A (SEA) and Dpt.

When living strains of the bacteria *Lactobacillus* and *Bifidobacterium* were preincubated with PBMCs, the resulting production of IL-4 by SEA and Dpt was greatly reduced compared with that that was triggered by the positive control (no preincubation with the *Lactobacillus* and *Bifidobacterium*). Interestingly, no significant suppression was observed when PBMCs were preincubated with the gram-negative control strains TG1 (FIG. 1). Although neither the four *Lactobacillus* and *Bifidobacterium* strains nor TG1 triggered basic IL-4 production, all four strains induced the production of IFN-γ. When PBMCs with SEA and Dpt were stimulated, the concentration of IFN-γ releases was, in addition, greatly increased. A synergistic effect was observed not only with the *Lactobacillus* and *Bifidobacterium* bacteria but also with TG1. Consequently *Lactobacillus* and *Bifidobacterium* appear capable of influencing both the secretion of $T_H1$ and of $T_H2$ cytokines in opposite directions.

The production of cytokines depends on time and dosage.

Figure 2:
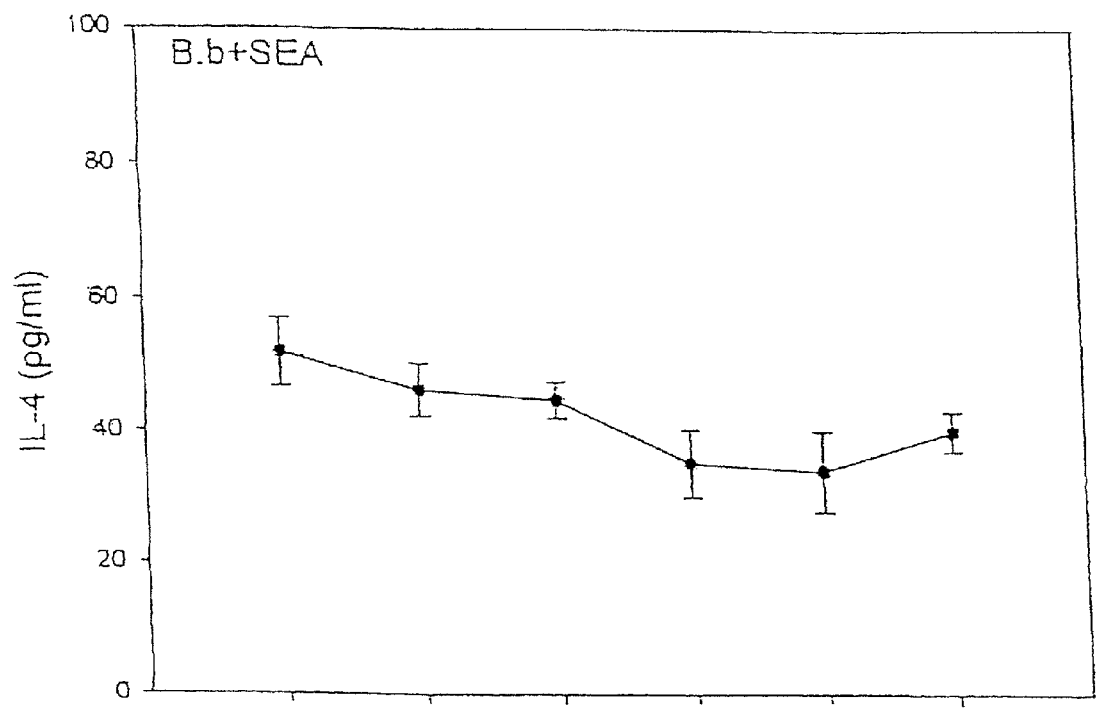
Figure 2:
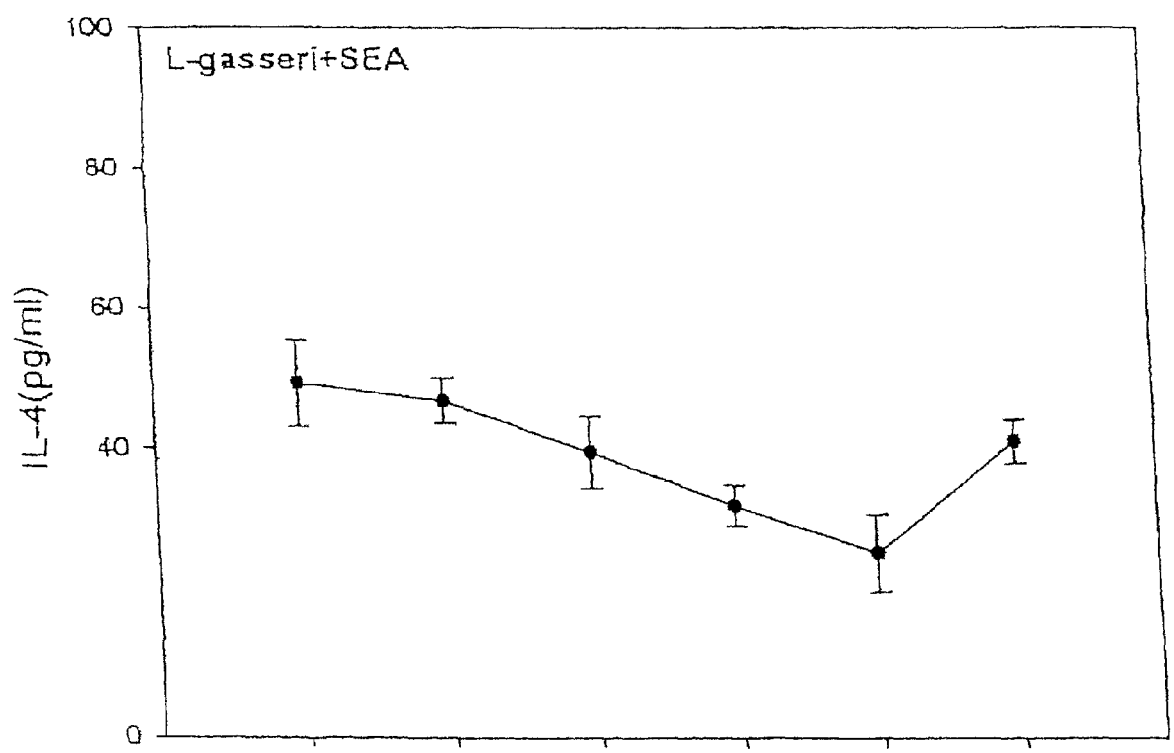
Figure 2:
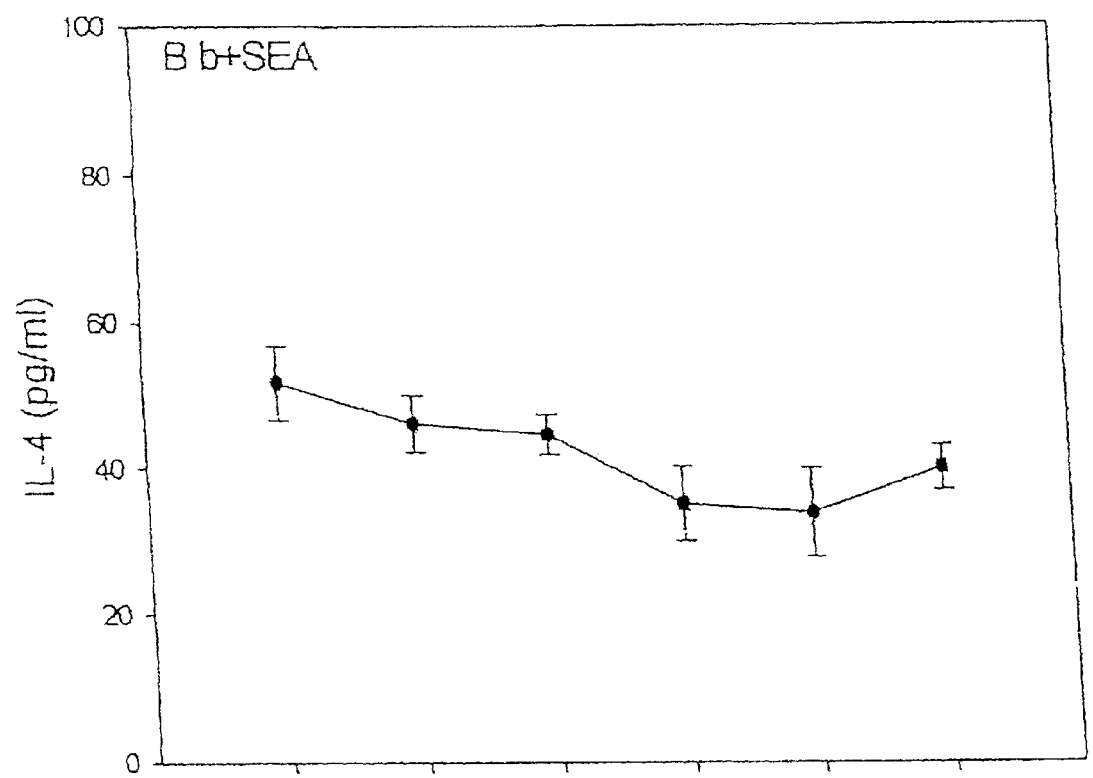
Figure 2:
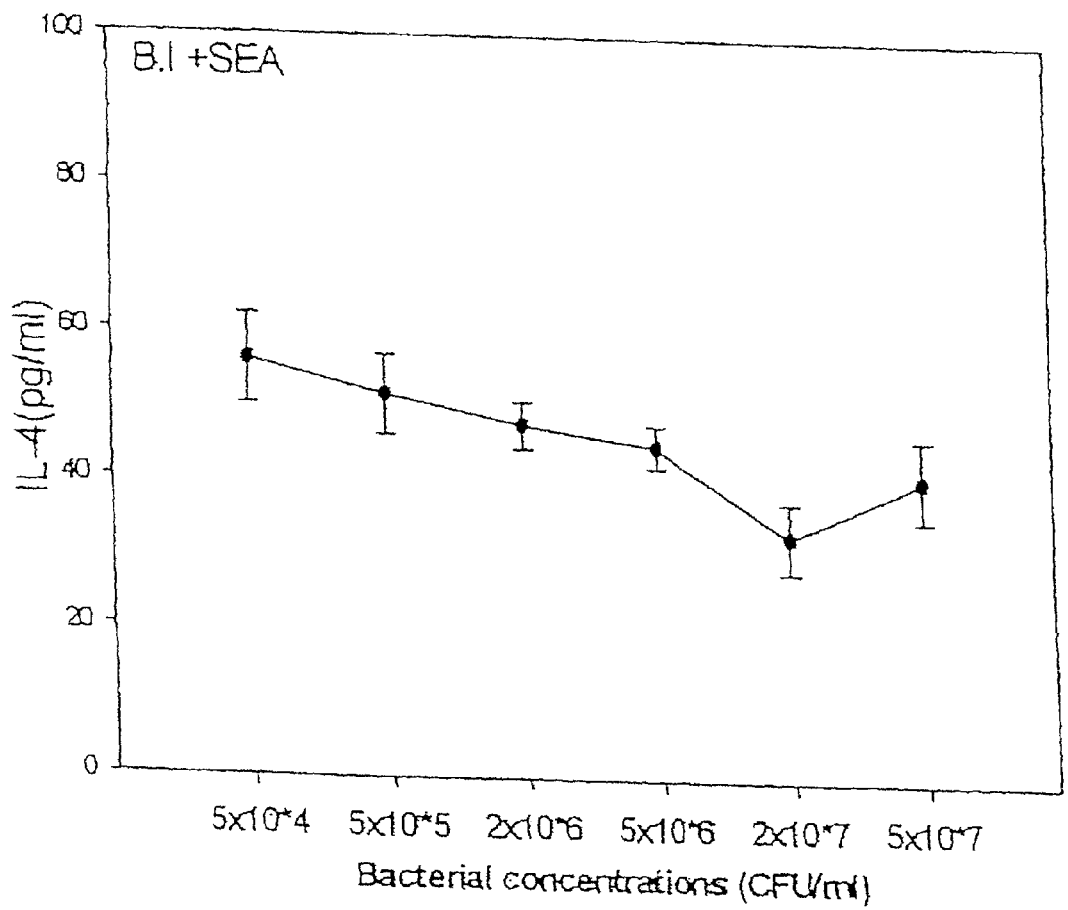
Figure 2:
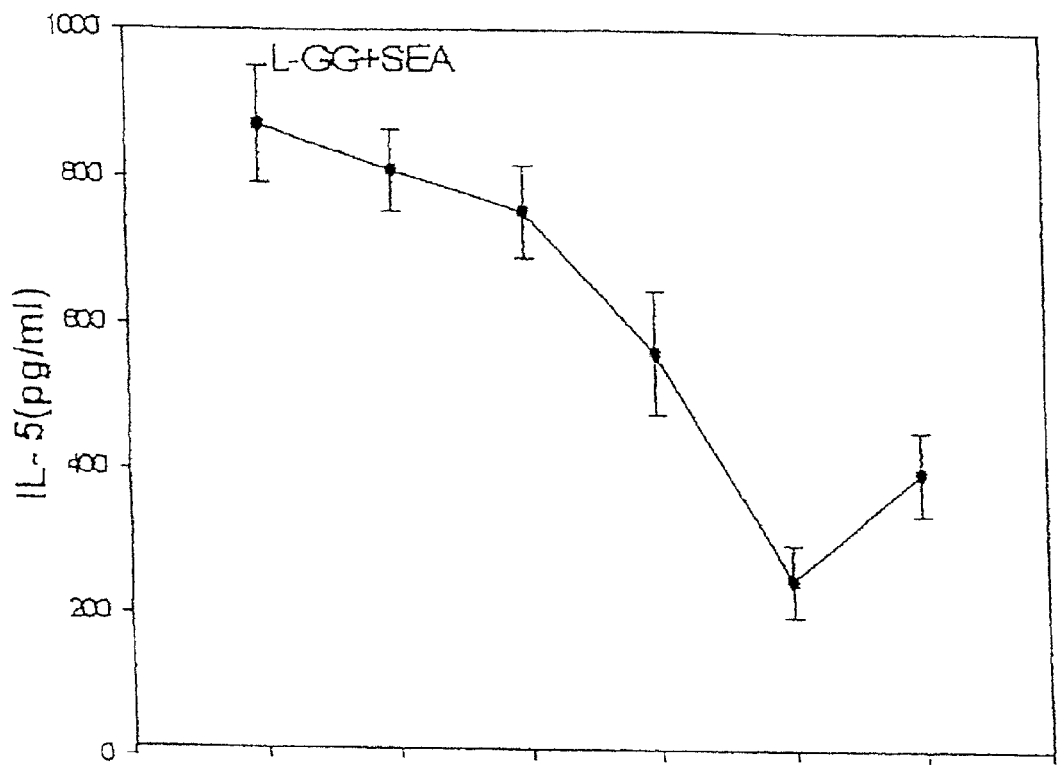
Figure 2:
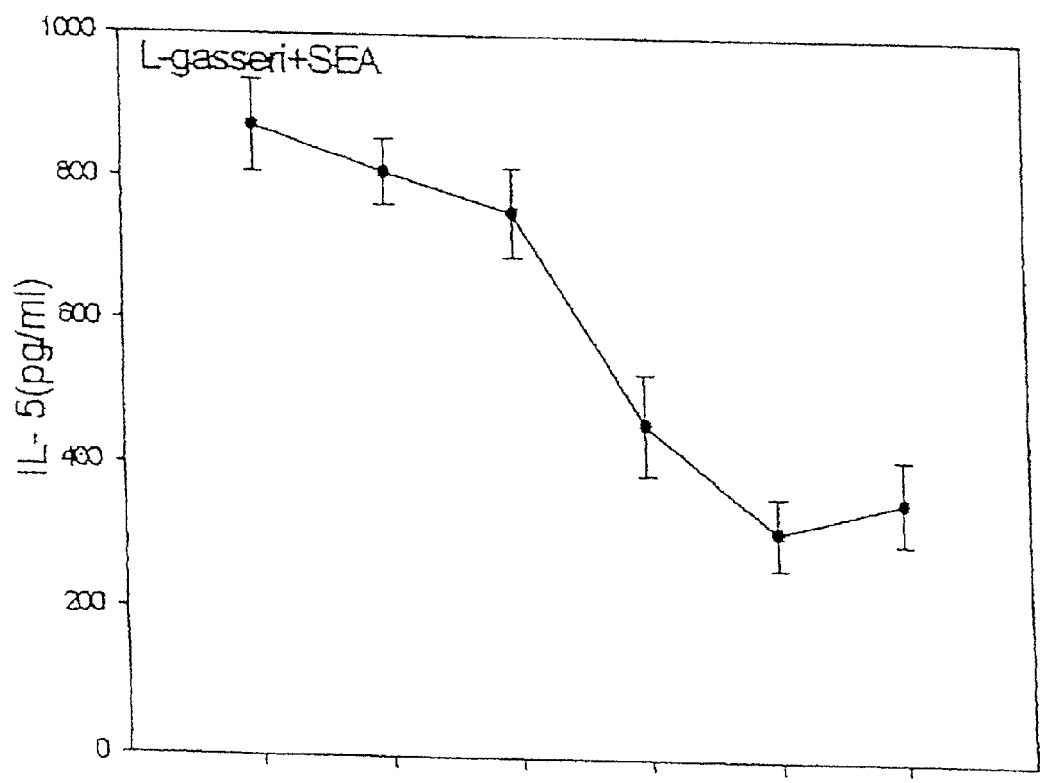
Figure 2:
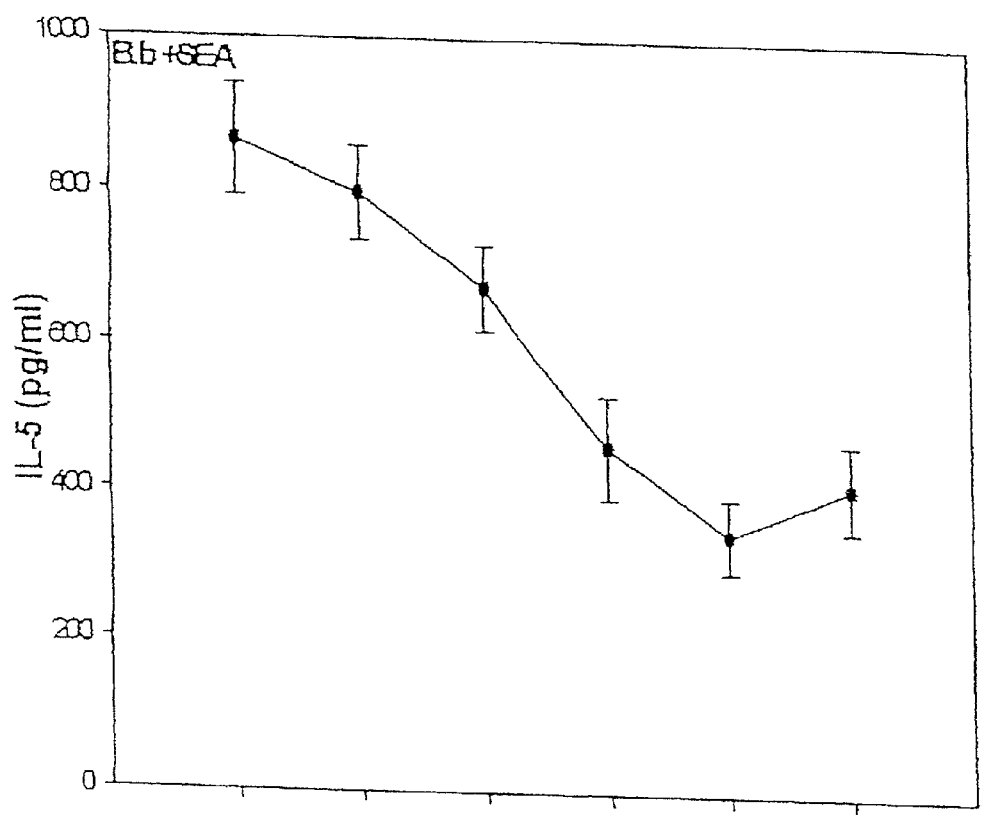
Figure 2:
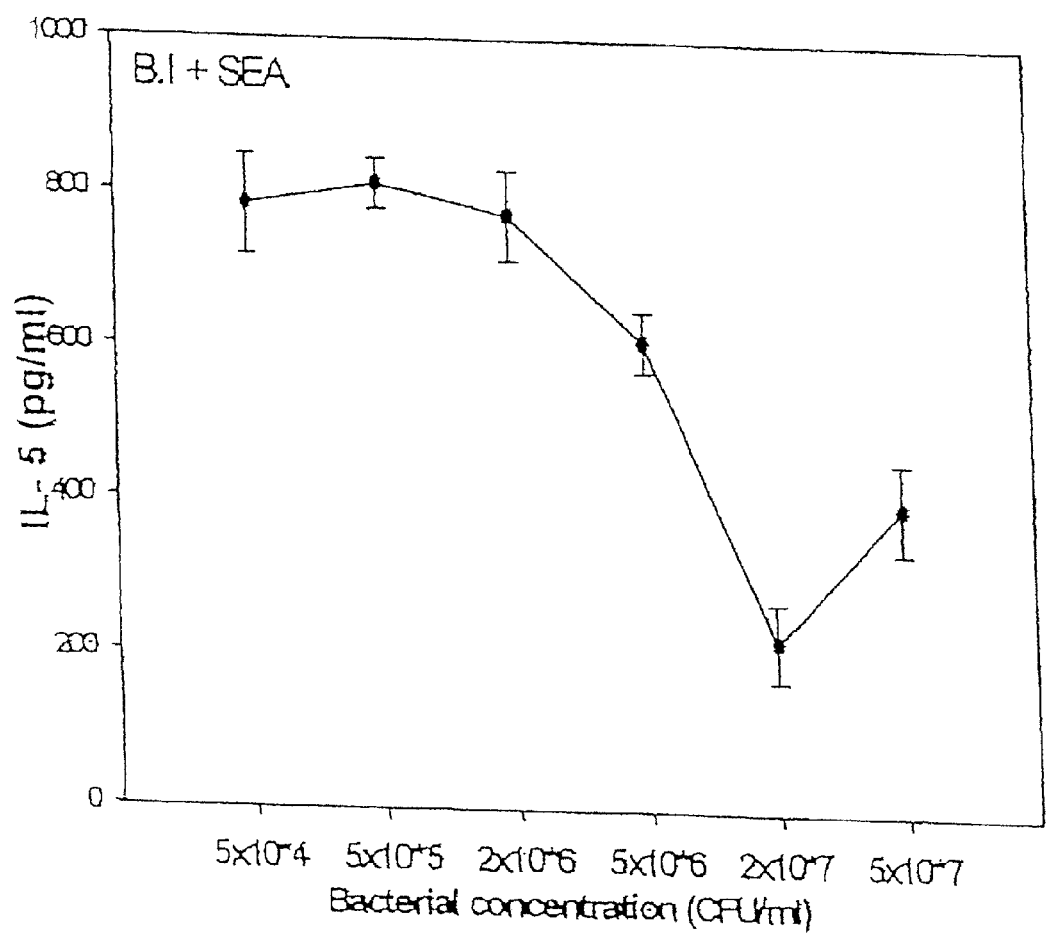
Figure 2:
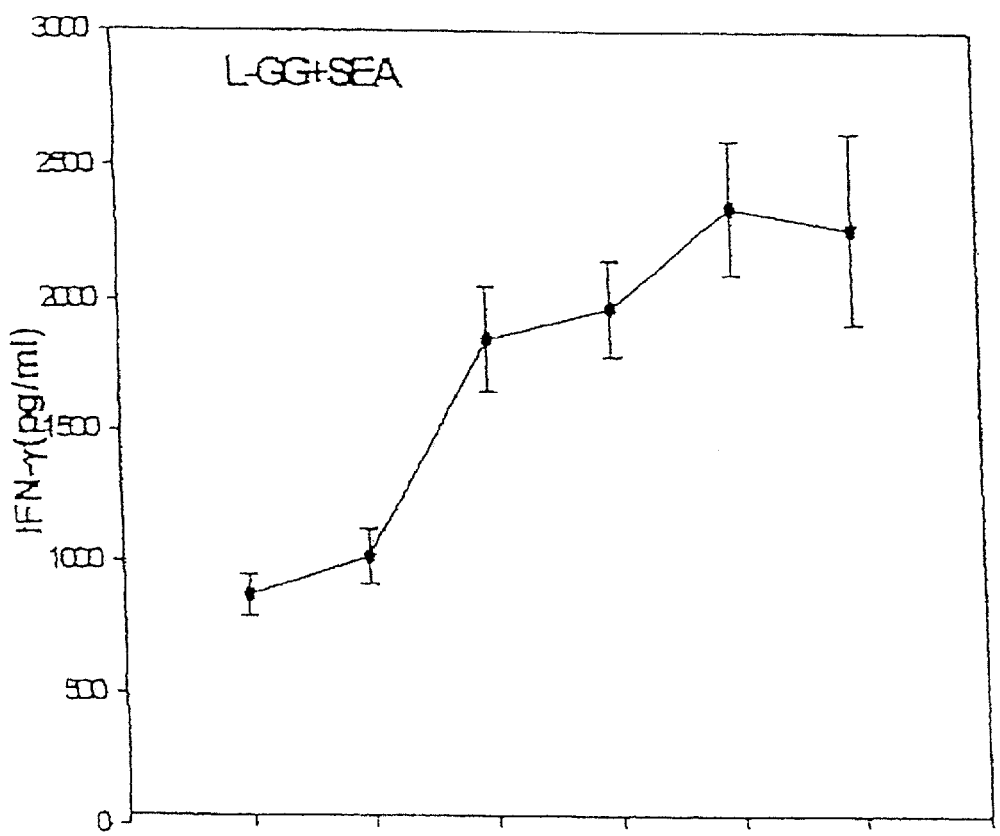
Figure 2:
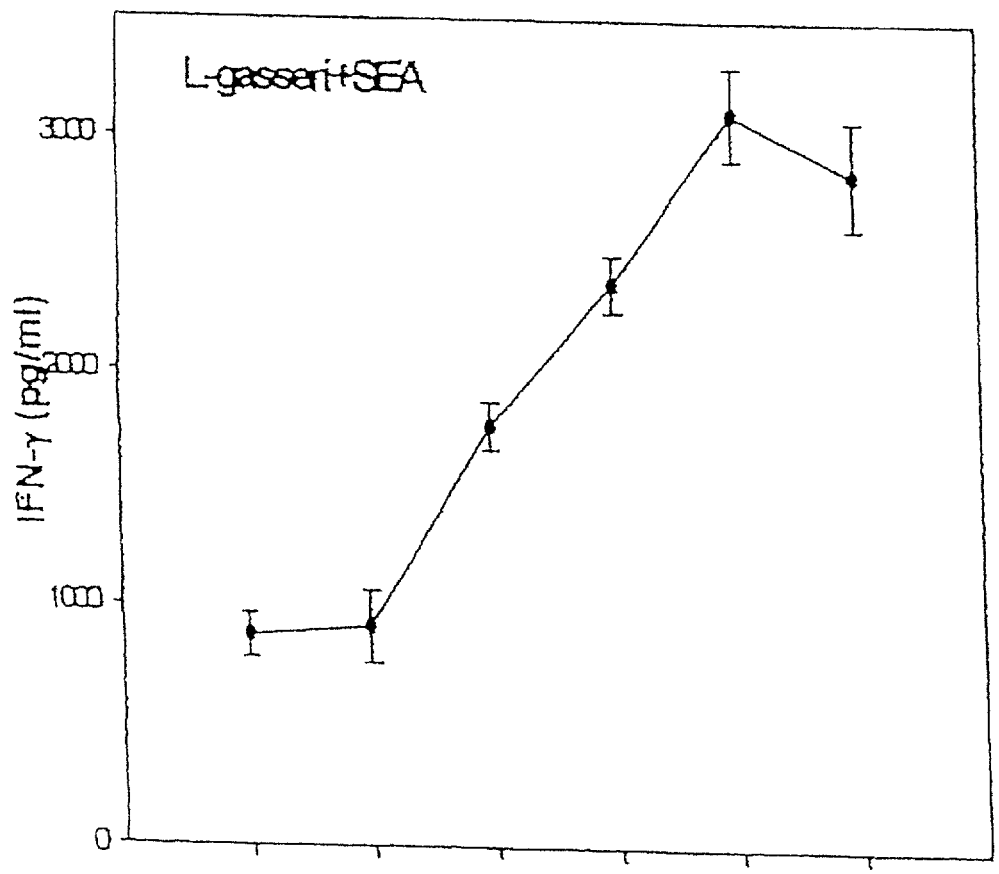
Figure 2:
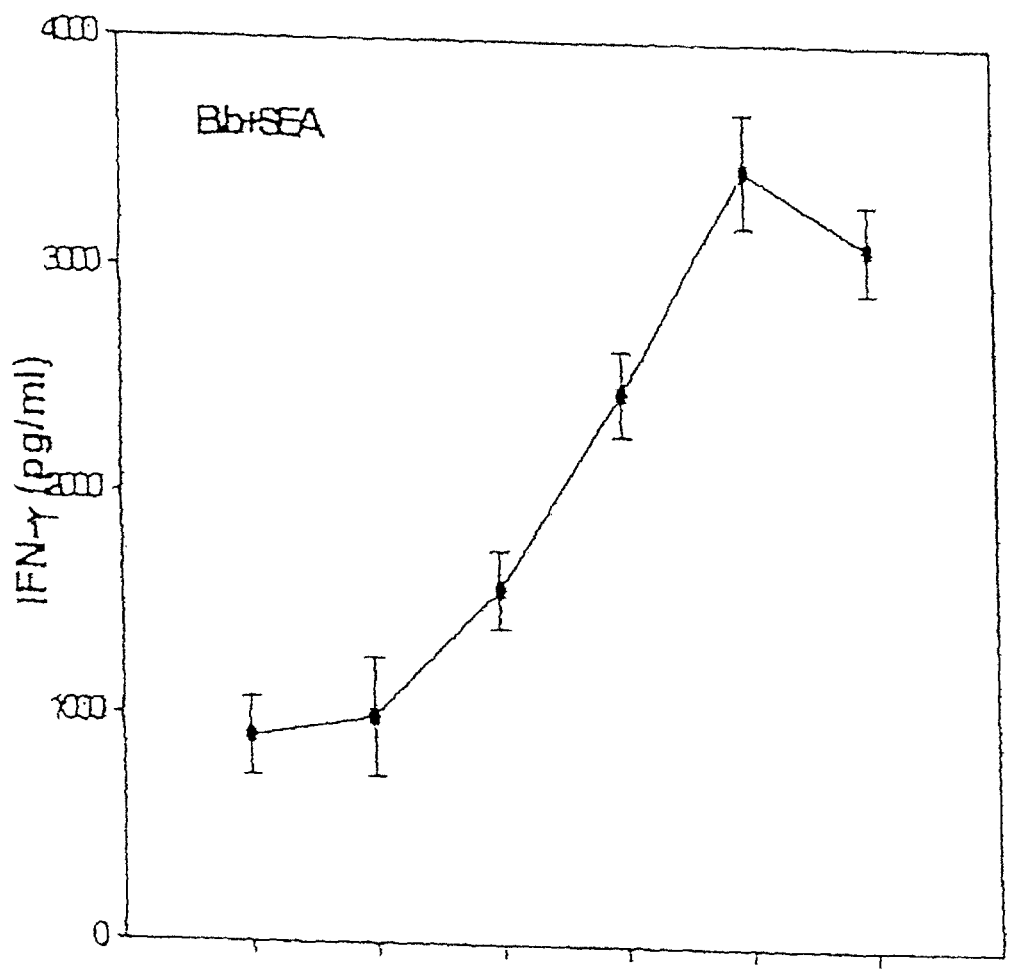
Figure 2:
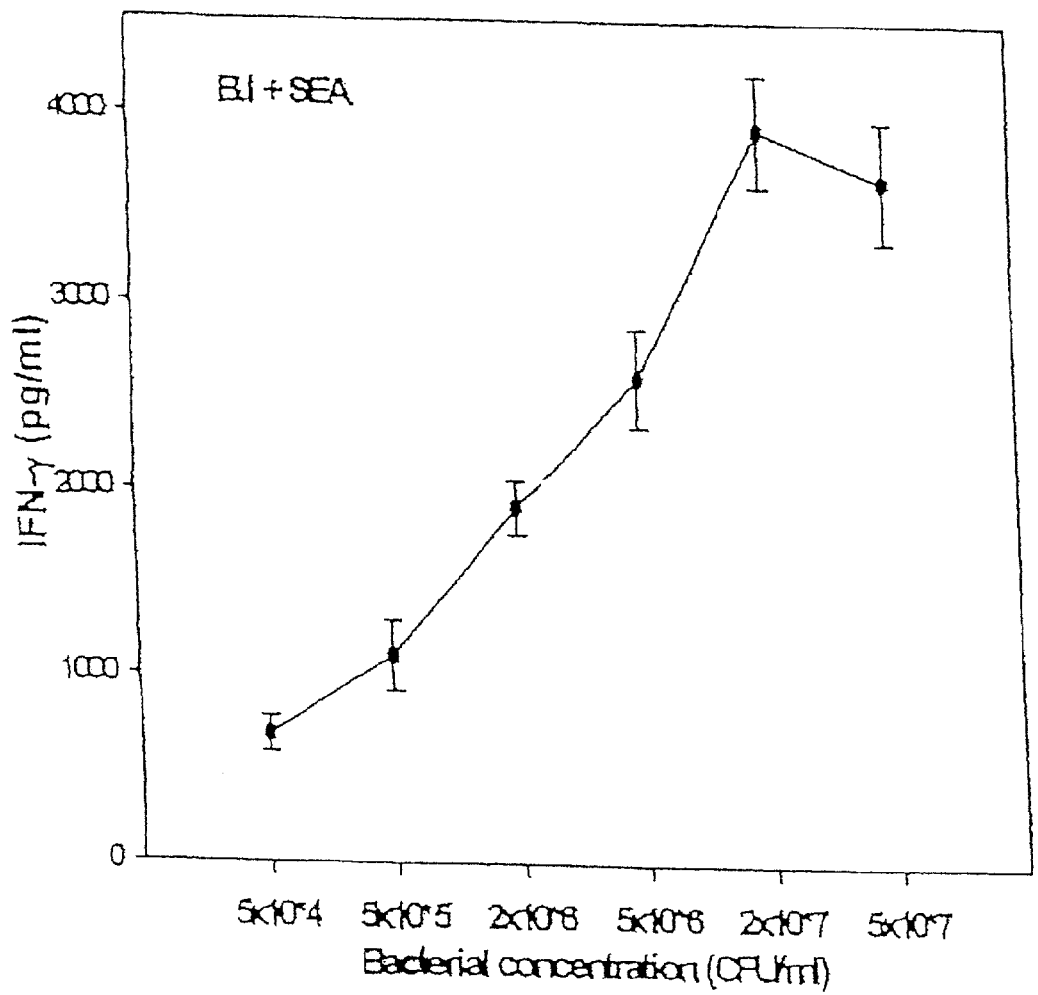

Other experiments performed with four *Lactobacillus* and *Bifidobacterium* strains showed that the suppression of $T_H2$ cytokines depends on time and dosage. When PBMCs were stimulated with probiotic bacteria before the addition of SEA, the growth inhibiting influence on the $T_H2$ cytokine production increases with the ratio of bacteria to PBMC. The maximum growth inhibition was observed at $2 \times 10^7$ CFU bacteria $ml^{-1}$, corresponding to a ratio of 10:1 (bacteria to BMC) (FIGS. 2, A and B).

This effect was also observed for the production of IL-4 and IL-5. For example, for the *L. gasseri* strains, the percentage of growth inhibition of the IL-4 production was raised from 40.19%±3% (1:1 ratio) to 54.22%±(10:1 ratio) in response to SEA. The percentage of the suppression of IL-5 production grew from 43.77%±8% (1:1 ratio) to 73.17%±5% (10:1 ratio). In addition, the percentage of inhibition of IL-4 production in response to Dpt in PBMC from healthy donors increased from 34.61%±4% (1:1 ratio) to 47.33%±5% (10:1 ratio). The percentage of the growth inhibition of IL-5 production grew from 45.72%±4% to 77.59%±6%. In contrast to $T_H2$ cytokine, our tested strains induced a basic production of IFN-γ, which appears to depend on the bacteria/cell ratio. It is remarkable that it has been possible to show that probiotic bacteria greatly influence the production of IFN-γ as a response to stimulation with SEA (FIGS. 1 and 2, C).

Time-Dependent Growth-Inhibiting Effect of Living Probiotic Bacteria on the Production of IL-4 and IL-5

PBMCs from healthy donors (n=4 at $2 \times 10^6$ $ml^{-1}$) were stimulated with SEA (2 μg/ml). Mononuclear cells were either preincubated for 1.3 and 5 hours with L. GG strains (10:1 ratio) before incubation before the SEA stimulation or they were simultaneously stimulated with the L. GG strains and the superantigen or L. GG was added 1.3 and 5 hours after the SEA stimulation, and the cell cultures were preincubated over a period of 24, 48 and 72 hours. At the aforementioned times, the cell-free supernatants were harvested and after centrifuging and sterilization stored at −20° C. The concentration of IL-4 and IL-5 were measured and showed that maximum growth suppression was observed for 3-hour preincubation of PBMCs with living bacteria before stimulation with SEA. Likewise, maximum growth inhibition was observed for 48-hour incubation (data not shown). This time-span was used in the further experiments.

*Lactobacillus* and *Bifidobacterium* suppress the production of $T_H2$ cytokines from allergen-stimulated PBMCs from allergic patients.

The capability of *Lactobacillus* and *Bifidobacterium* to correct the imbalance between $T_H1$ and $T_H2$ cytokines was then evaluated in an even more relevant model of stimulation by allergens. When PBMCs from patients (allergic to *D. pteronyssinus*) were preincubated with various viable strains of *Lactobacillus* and *Bifidobacterium*, the production of IL-4 and IL-5 triggered after specific stimulation with *D. pteronyssinus* allergens was greatly reduced, specifically in a manner dependent on the bacteria/cell ratio. This effect on IL-5 was independent of the type of strain of the investigated probiotic bacteria. The suppression of IL-5 corresponded, for example in the case of B.b., to 57.31%±4.52% and in the case of B.l. to 63.77%±5% (FIG. 1) Furthermore, similar effects were observed when PBMCs from allergic patients were stimulated with SEA. In this case, although IL-4 and IL-5 production were very high in comparison to the production that was observed with *D. pteronyssinus* (FIG. 1), the tested probiotic bacteria reduced the secretion of IL-5 by 71.29%±4.10% for L. GG and 77.63%±3.52% for *L. gasseri* (FIG. 1). Coincubation with *Lactobacillus* and *Bifidobacterium* greatly increased the production of IFN-γ (FIG. 1). In this manner, by the reduction of the production of $T_H2$ cytokines and by the intensification of IFN-γ production of PBMCs from allergic patients, *Lactobacillus* and *Bifidobacterium* appear to show anti-$T_H2$ activity. In this context, it is interesting to note that the growth-inhibiting effect of *Lactobacillus* and *Bifidobacterium* on IL-4 production by PBMCs from allergic test subjects is greater than for healthy test subjects. In contrast to this, the growth-inhibiting effect of these bacteria on IL-5 production by PBMC from healthy donors is greater than for allergic test subjects (FIG. 1). In contrast to this, the growth-inhibiting effect of B.l and LgsBbBl on IL-4 production by Dpt-stimulated PBMC from allergic test subjects was greater than that from healthy test subjects (p<0.05) and the inhibiting effect of L. GG, B.b. and B.l on IL-4 production by SEA-stimulated PBMC from allergic test subjects was greater than for healthy test subjects (p<0.01). In contrast to this, the growth-inhibiting effect of *L. gasseri*, B.b and B.l on IL-5 production by Dpt-stimulated PBMC from healthy test subjects was greater than for allergic test subjects (p<0.05) and the suppressing effect of LgsBbBl on IL-5 production from SEA-stimulated PBMC from healthy test subjects was greater than for allergic patients (p<0.01, FIG. 1).

Genomic DNA from probiotic bacteria inhibits the production of IL-4 and IL-5 by SEA-stimulated PBMC from healthy test subjects depending on the time and dosage.

Figure 4:
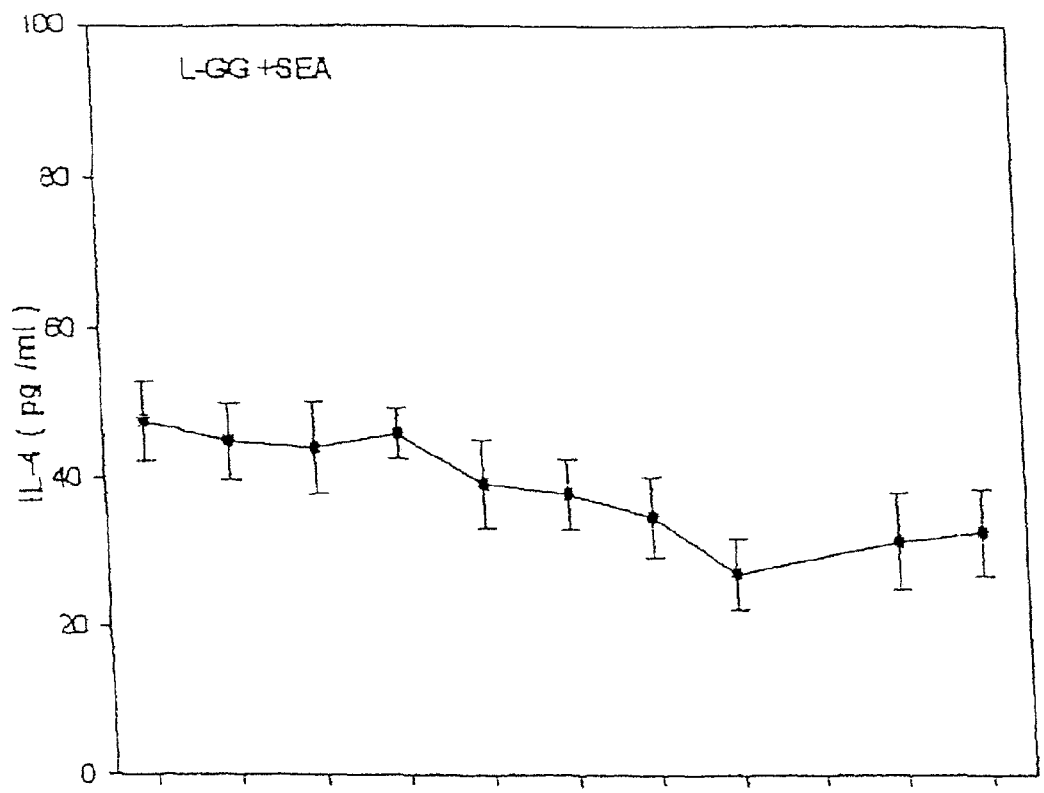
Figure 4:
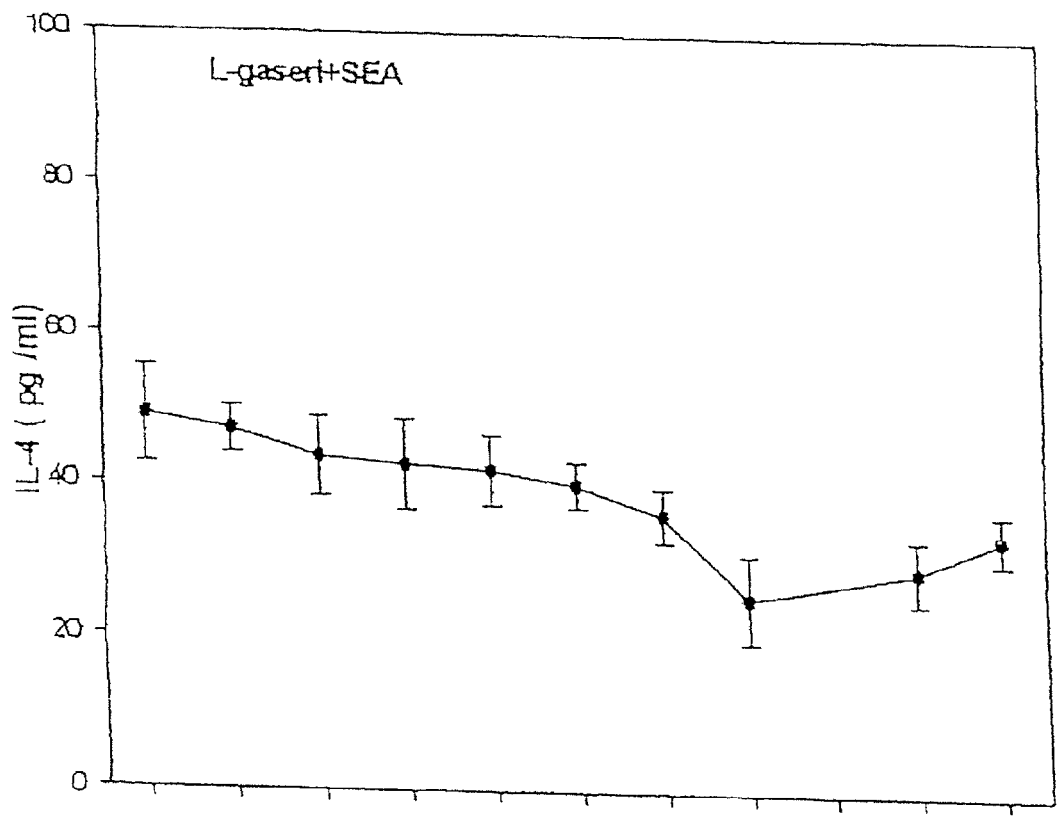
Figure 4:
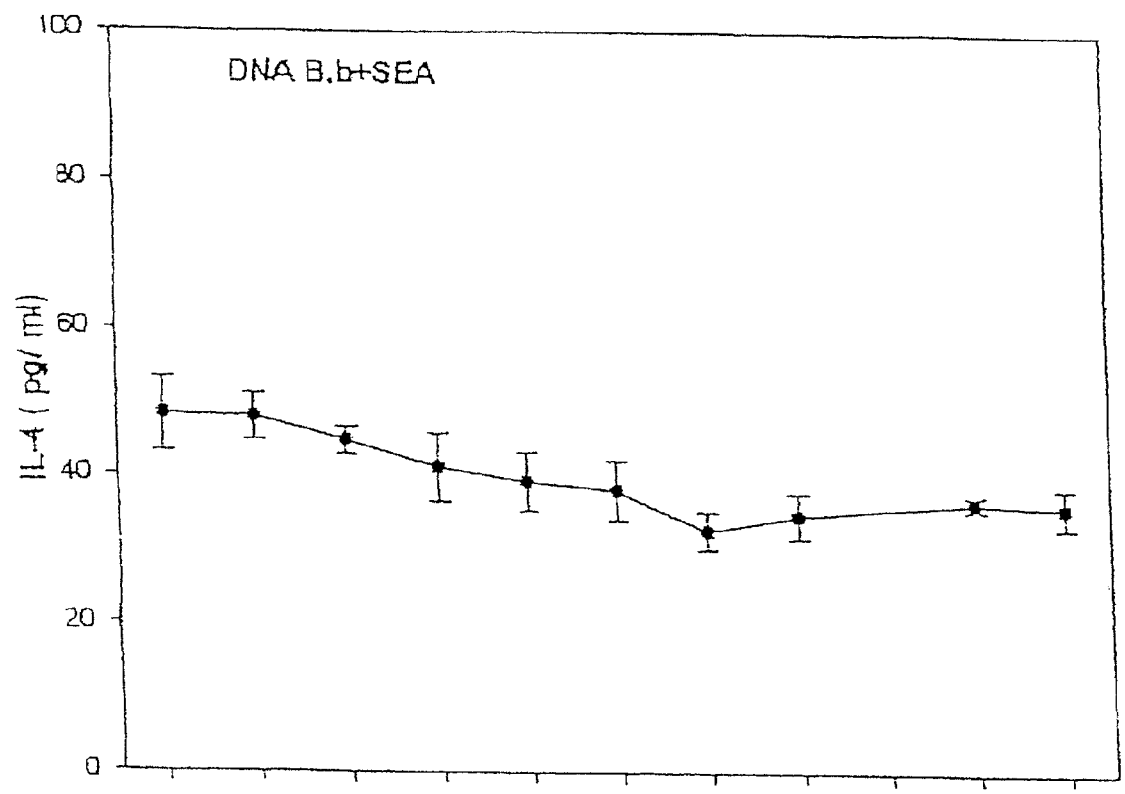
Figure 4:
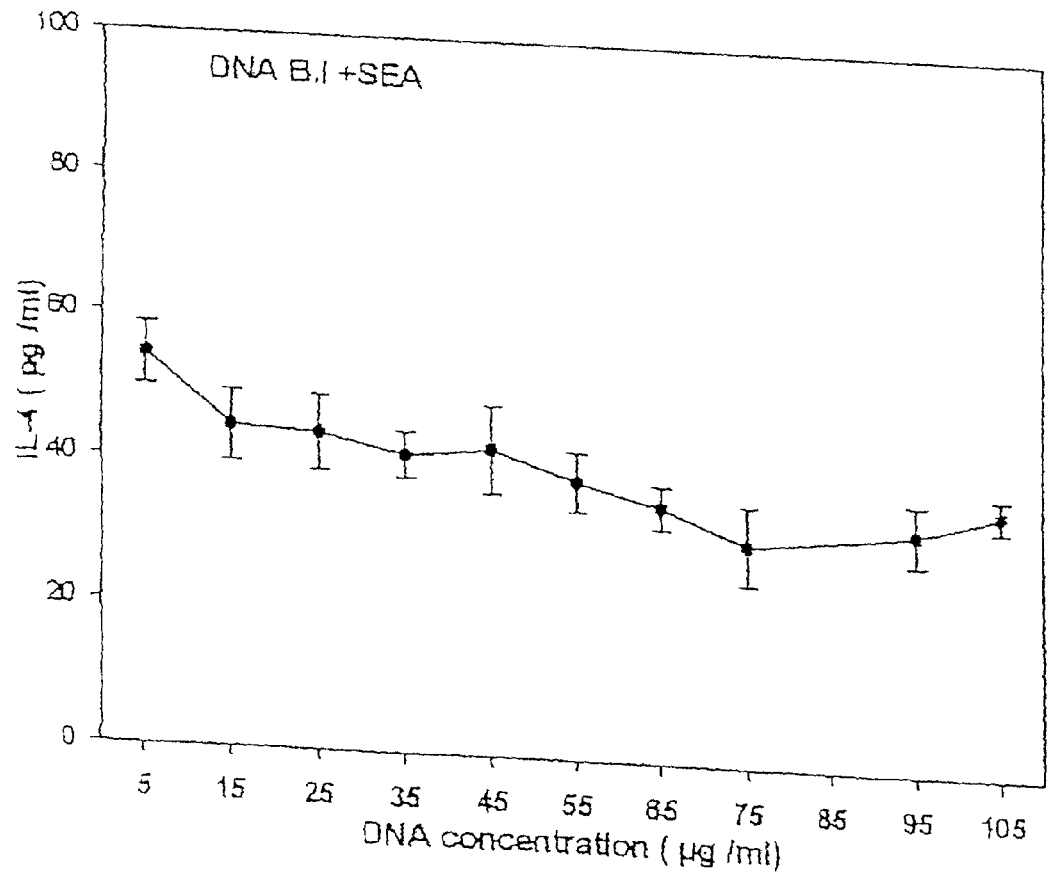
Figure 4:
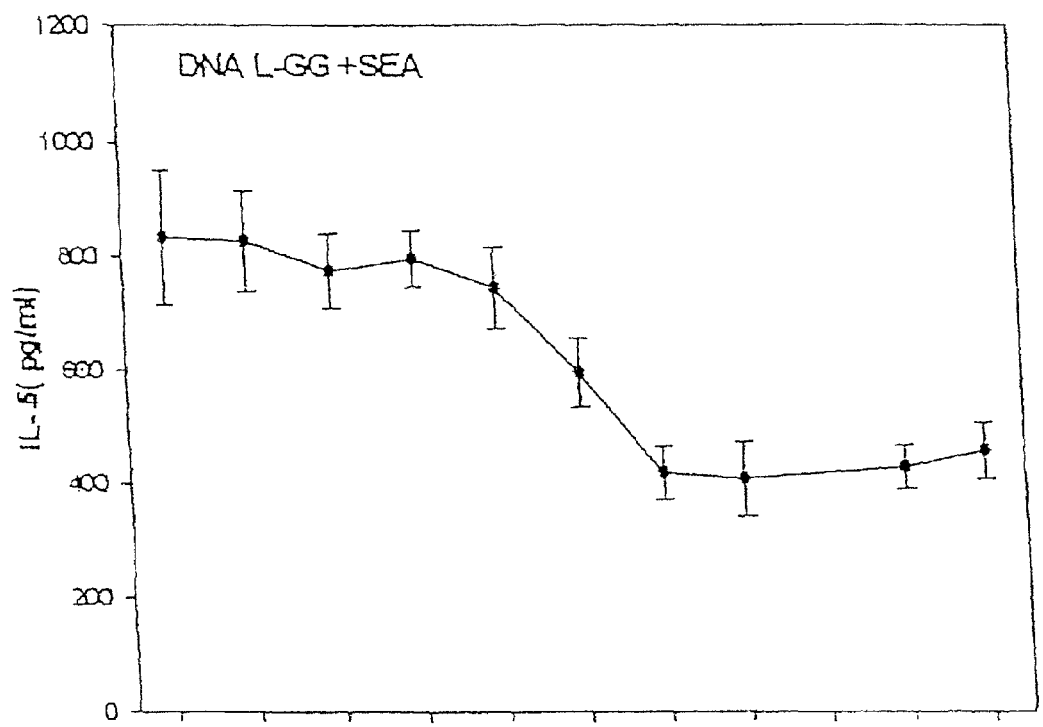
Figure 4:
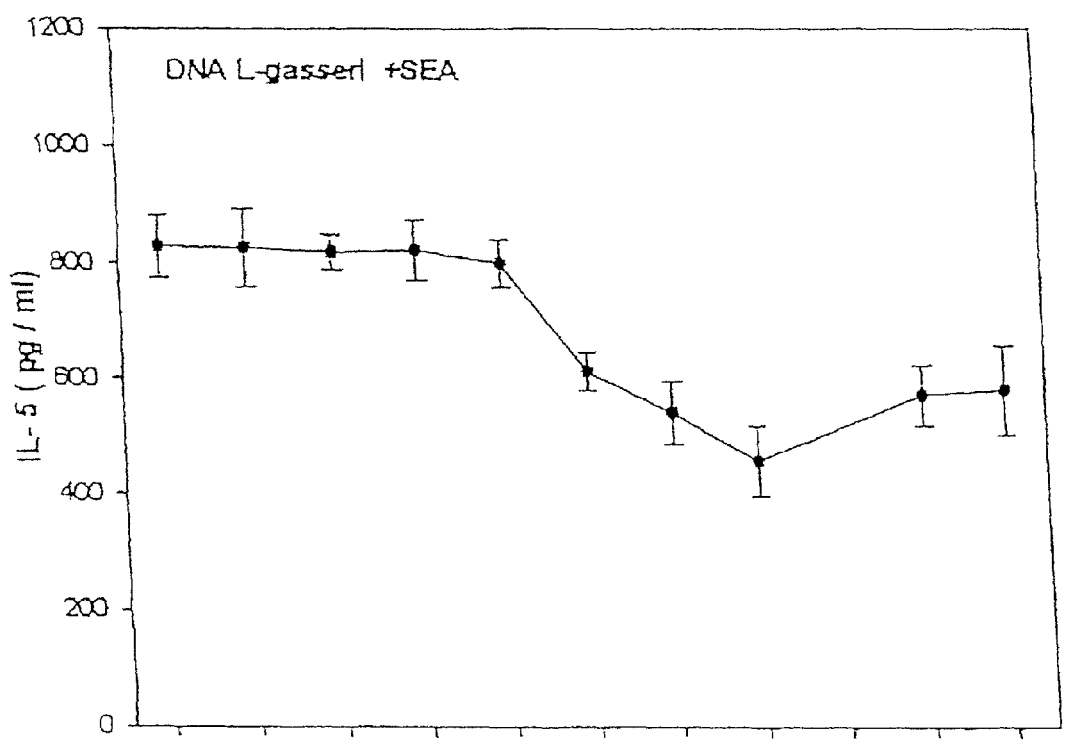
Figure 4:
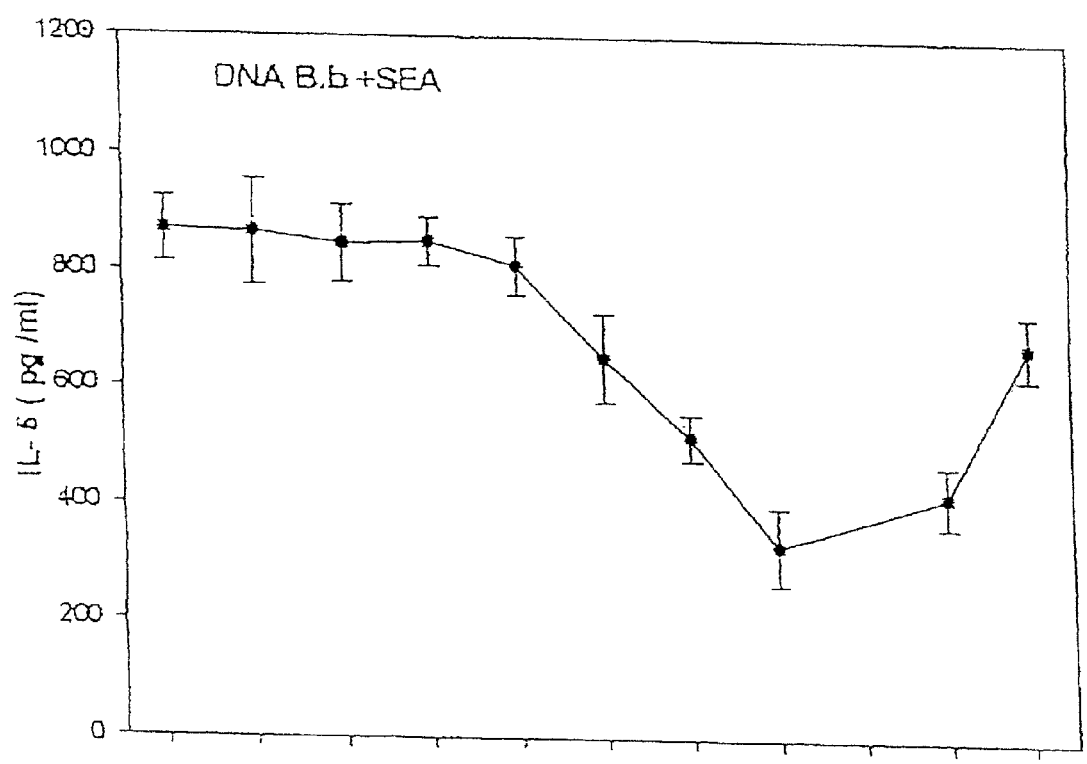
Figure 4:
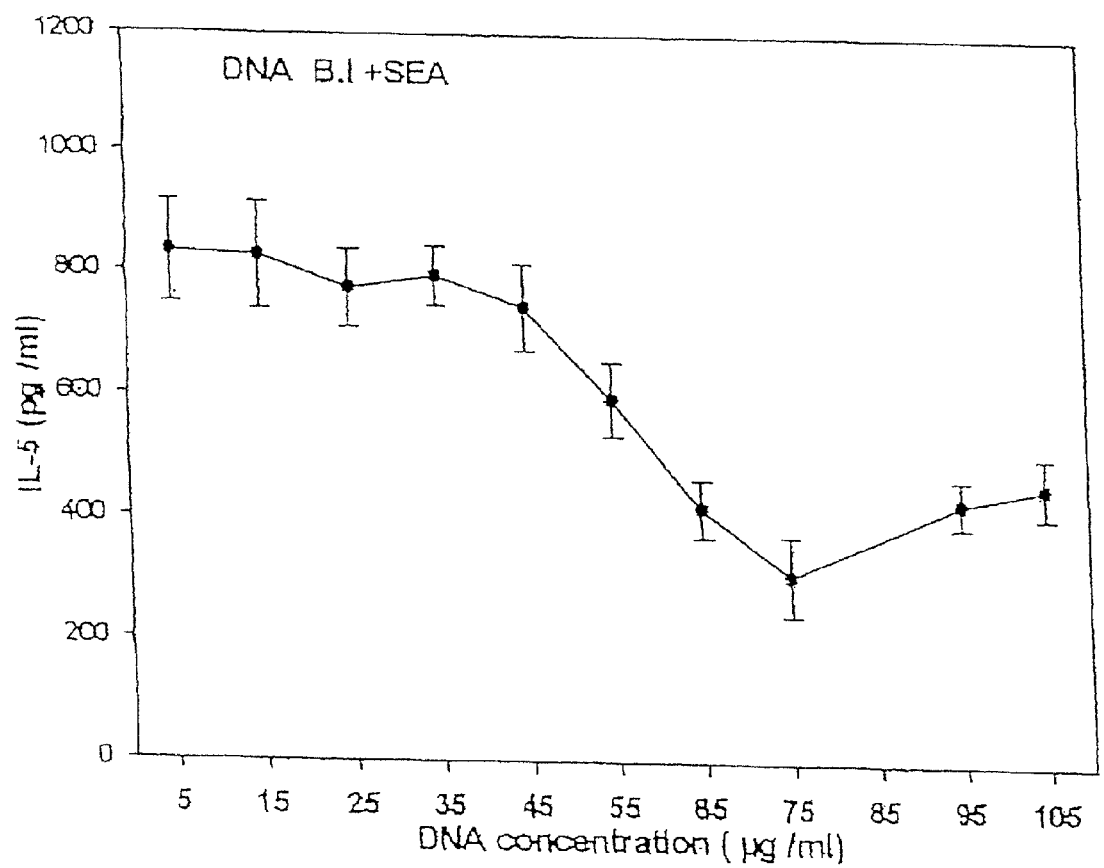
Figure 4:
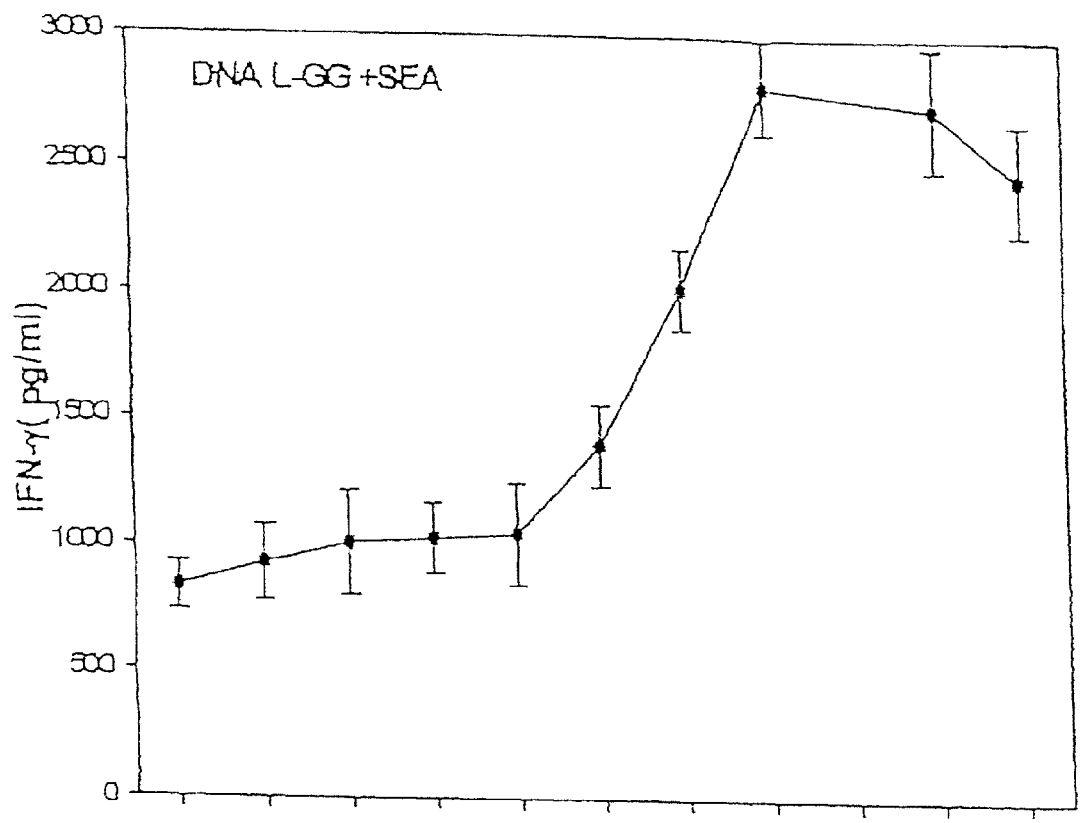
Figure 4:
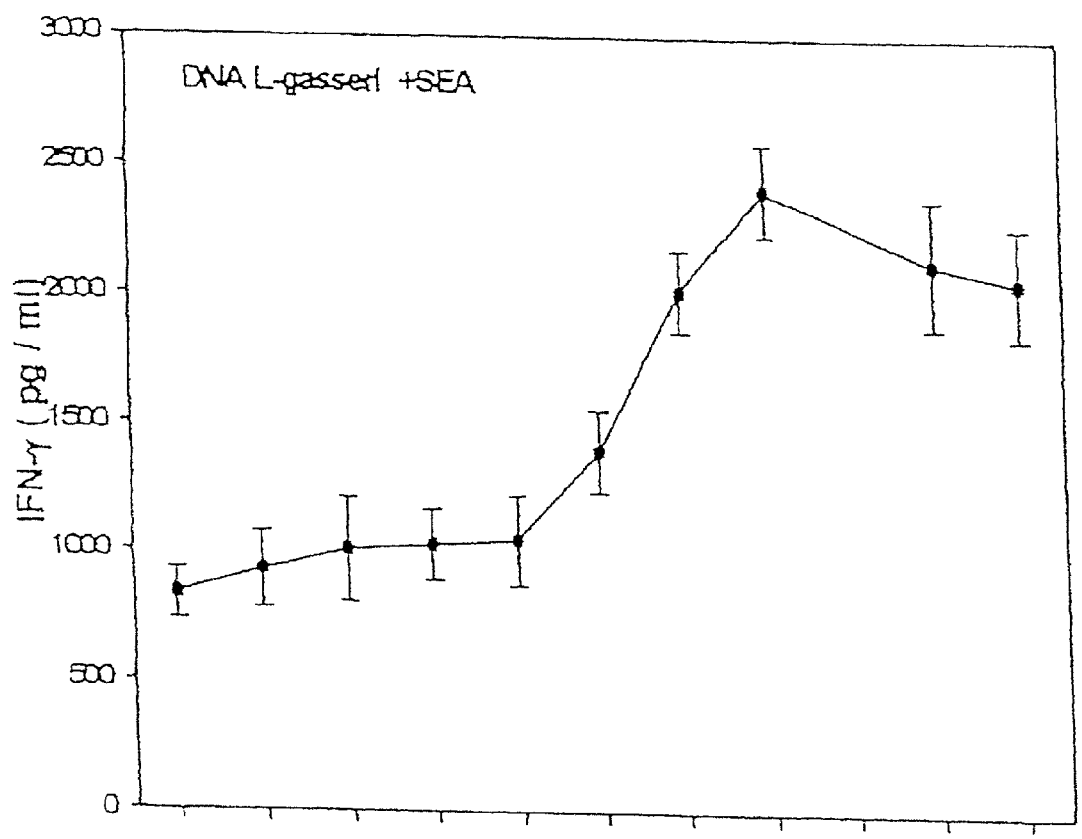
Figure 4:
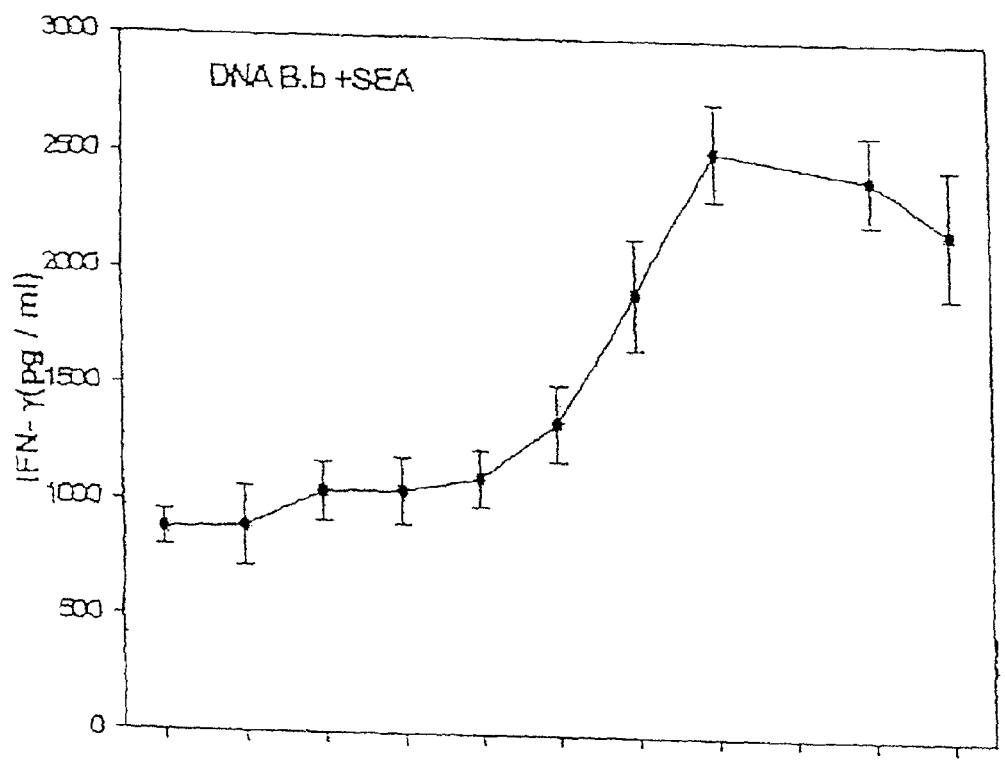
Figure 4:
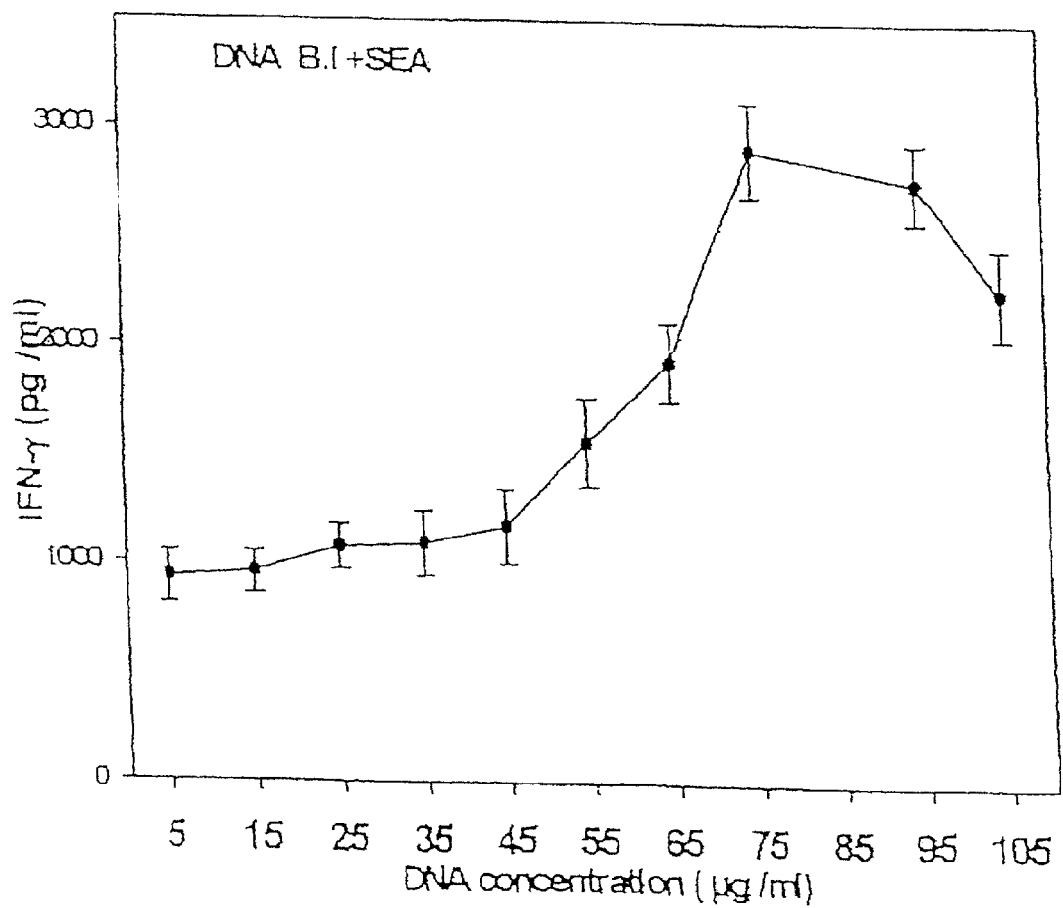

To estimate the growth inhibiting effect of bacterial DNA in comparison to animal DNA and LPS, PBMCs from four healthy test subjects were incubated with genomic DNA from four strains of probiotic bacteria, L. GG, *L. gasseri*, B.b, B.l and LgsBbBl (a mixture of *L-gasseri*, B.b. and B.l), LPS and animal DNA (calf thymus DNA). The suppression of $T_H2$ cytokines was monitored by the application of BDoptEIA test sets to demonstrate and quantify the production of cytokines. As shown in FIG. 4, the DNA from probiotic bacteria normally prevents the PBMCs from producing IL-4 and IL-5 as a response to stimulation by SEA or Dpt. In contrast to this, LPS did not reduce the production of IL-4 and IL-5; likewise the LPS-free calf thymus DNA did not reduce the production of IL-4 and IL-5 (data not shown).

Time-Dependent Growth-Inhibiting Effect of Bacterial DNA on the Production of IL-4 and IL-5 by SEA-Stimulated PBMC from Healthy Test Subjects Some experiments were performed to determine the time profile of the response to genomic DNA. PBMCs from healthy donors (n=4, at $2\times10^6$ ml$^{-1}$) were stimulated with SEA (2 μg ml$^{-1}$) and were either preincubated for one, three and six hours with genomic DNA from the L. GG or B.b. (30 μg ml$^{-1}$) before SEA stimulus, or were stimulated simultaneously with genomic DNAs. Superantigen or genomic DNAs were added 1, 3 and 6 hours after the SEA stimulus and cell cultures were incubated over periods of 24, 48 and 72 hours. The genomic DNA from L. GG and B.b. was selected as representative for the two Lactobacillus and Bifidobacterium strains. At the aforementioned times, the cell-free supernatants were harvested and, after centrifuging and sterilization, were stored at −80° C. The concentrations of IL-4 and IL-5 were measured and showed that maximum growth suppression was observed at $t_0$ hours of the incubation of PBMCs with genomic DNAs and SEA (data not shown), likewise the maximum suppression was reached after 24 hours' incubation. This time was used for further experiments. Genomic DNA from B.b. was confirmed as a more effective inhibitor of IL-4 than genomic DNA from L. GG. In contrast to this, it was confirmed that genomic DNA from L. GG was a more effective inhibitor of IL-5 than genomic DNA from B.b.

Dosage-Dependent Growth-Inhibiting Effect of Bacterial DNA on the Production of IL-4 and IL-5 from SEA-Stimulated PBMCs from Healthy Test Subjects To investigate the growth-inhibiting effect of bacterial DNA on the inhibition of IL-4 and IL-5 by SEA-stimulated PBMC from healthy test subjects, the genomic DNA from each strain was introduced into the PBMC culture in various concentrations, specifically in the range from 5 to 105 μg ml$^{-1}$ to determine which dosage has the greatest inhibiting effect on IL-4 and IL-5 production (FIG. 4). This dosage range was chosen on the basis of the test results described above, which showed that the production of cytokines by immune cells could be demonstrated after the addition of at least 3 μg ml$^{-1}$ E. coli. DNA and the optimum stimulation required a bacterial DNA in a concentration of >50 μg ml$^{-1}$. As shown in FIG. 4, the maximum inhibition of IL-4 and IL-5 was observed when genomic DNA was used in a concentration of 75 μm gl$^{-1}$. Three different patterns of cytokine responses could be clearly differentiated.

Genomic DNA: All strains suppressed the production of IL-4 and IL-5 at a concentration of 75 μg ml$^{-1}$ with the exception of B.b.-DNA and L. GG-DANN, which suppressed the production of EL-4 and EL-5 at a concentration of 65 μg ml$^{-1}$.

All genomic DNAs suppressed the production of IL-4 and IL-5 to lower, steady-state levels when they are added in a concentration range from 5 to 45 μg ml$^{-1}$. In contrast to this, all genomic DNAs showed a dosage-dependent intensification of IL-4 and IL-5 production when they were used in a concentration range from 85 to 105 μg ml$^{-1}$. In comparison to the other genomic DNAs, B.b and L. GG DNAs appear to be more efficient inhibitors of IL-4 and IL-5 production in response to SEA stimulation. Furthermore, the genomic DNA from B.b showed the lowest inhibiting influence on IL-5 production at a concentration of 105 μg ml$^{-1}$.

Growth-Inhibiting Effect of Genomic DNA from Probiotic Bacteria on the Production of IL-4 and IL-5 by SEA-Stimulated PBMC from Allergic Test Subjects To research the growth-inhibiting effect of genomic DNA from probiotic bacteria, PBMC ($2\times10^6$ ml$^{-1}$) at 75 μg ml$^{-1}$, from L. GG DNA, BI DNA and LgsBbBl, DNA was incubated for 24 hours. Three different patterns of the inhibition of IL-4 production as a response to SEA stimulation could be clearly distinguished: genomic DNAs from L-GG and LgsBbBl showed the strongest inhibiting effect, namely 37.4%±4% and 39.56%±5.1% respectively. L. gasseri DNA showed the lowest inhibiting effect (19.14%±2%) and B.b. B.l. showed a similar pattern (24.47%±3.28%). Conversely, L. gasseri DNA shows the greatest growth-inhibiting effect on IL-5 production as a response to SEA stimulation (61.41%±3.74%), LgsBbBl DNA showed the lowest suppression (46.31%±4%) and genomic DNA from L. GG, B.b. and B.i. showed an identical suppression pattern, (data not shown). Furthermore, we compared the inhibiting effect of genomic DNAs with living bacteria, as well as the suppressing effect of genomic DNA on IL-4 and IL-5 production as a response to SEA stimulation between healthy and allergic test subjects. The growth-inhibiting effect of living bacteria on IL-4 production by healthy and allergic test subjects is higher than the influence of their genomic DNA. In contrast to this, the growth-inhibiting effect of genomic DNA in allergic test subjects is greater than in healthy test subjects (with the exception of L. gasseri). Consequently, genomic DNAs are more effective in reducing IL-4 production as a response to SEA stimulation in allergic test subjects.

In summary, the growth-inhibiting effect of living bacteria on IL-5 production as a response to SEA stimulation in PBMCs from healthy and allergic patients is the same as the effect on IL-4 production (e.g. the inhibiting effect of living bacteria was higher than that of their genomic DNA in both healthy and allergic test subjects). But the growth-inhibiting effect of genomic DNAs on IL-5 production in healthy donors was greater than for allergic test subjects.

Consequently, genomic DNAs are more effective inhibitors for IL-5 in healthy donors. With respect to Dpt stimulation, the inhibiting effect of genomic DNA from L. GG and LgsBbBl on IL-4 production by Dpt-stimulated PBMC from allergic test subjects was greater than in the case of healthy test subjects (p>0.05). A similar pattern was obtained for genomic DNA from L. gasseri B. b and B. l.

Figure 3:
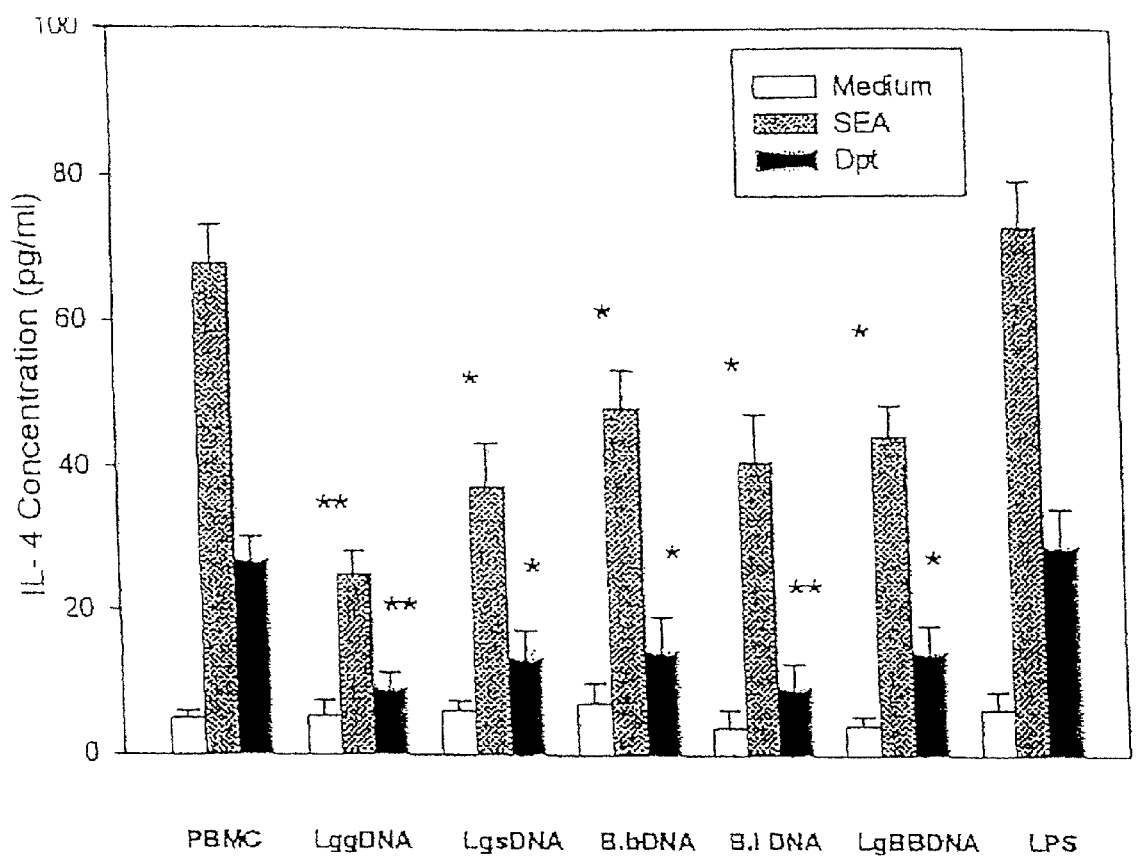
Figure 3:
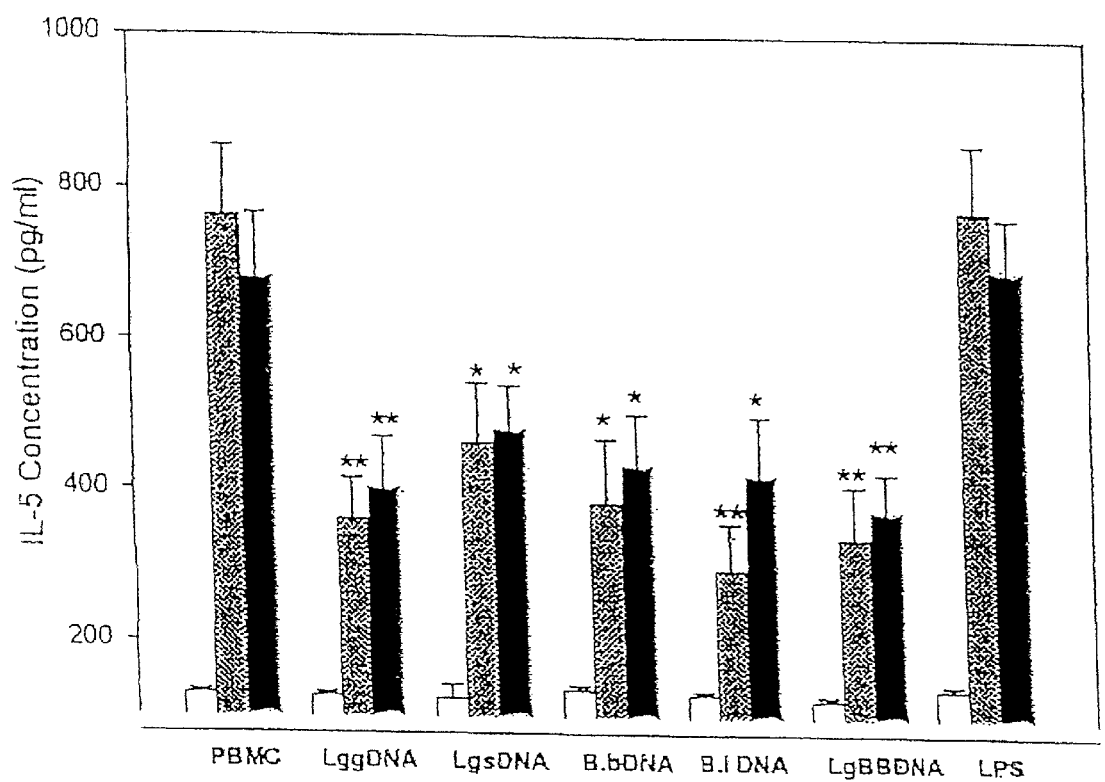
Figure 3:
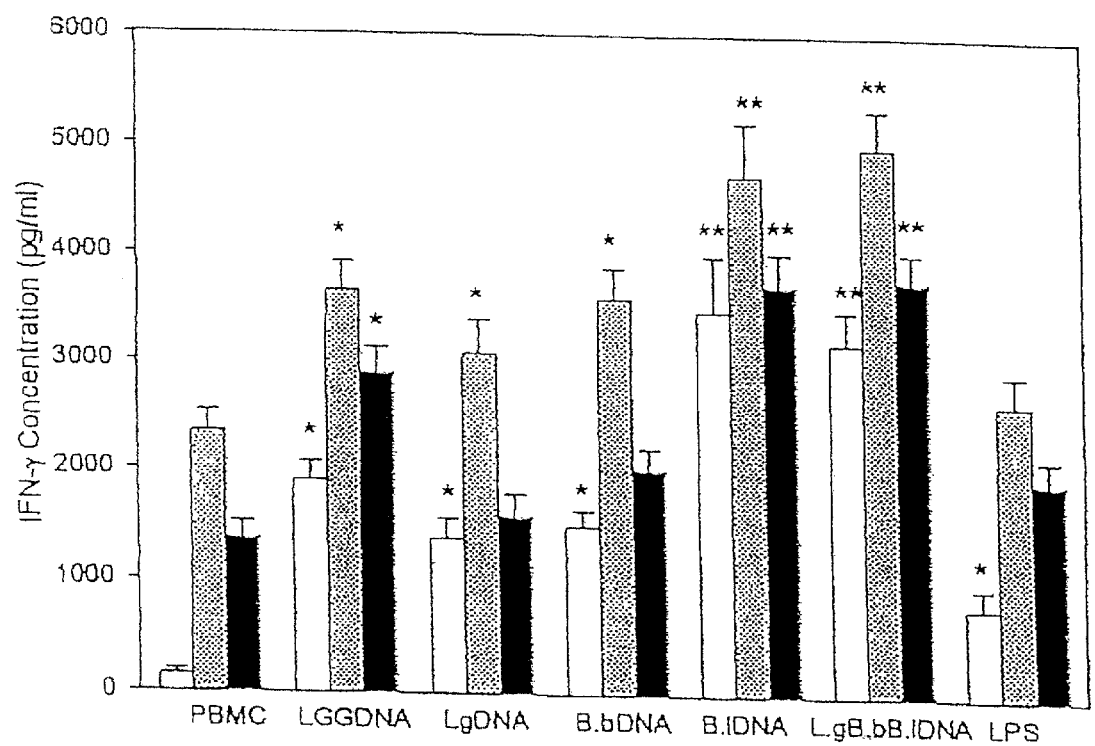
Figure 3:
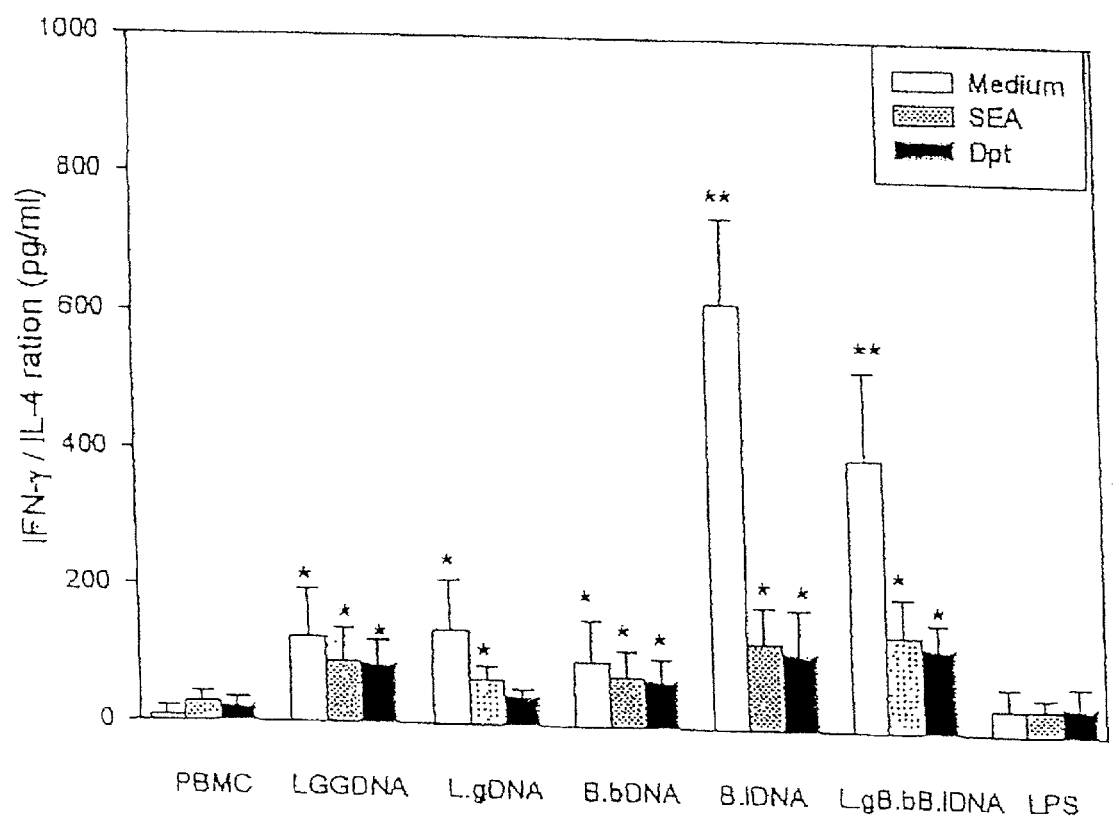
Figure 3:
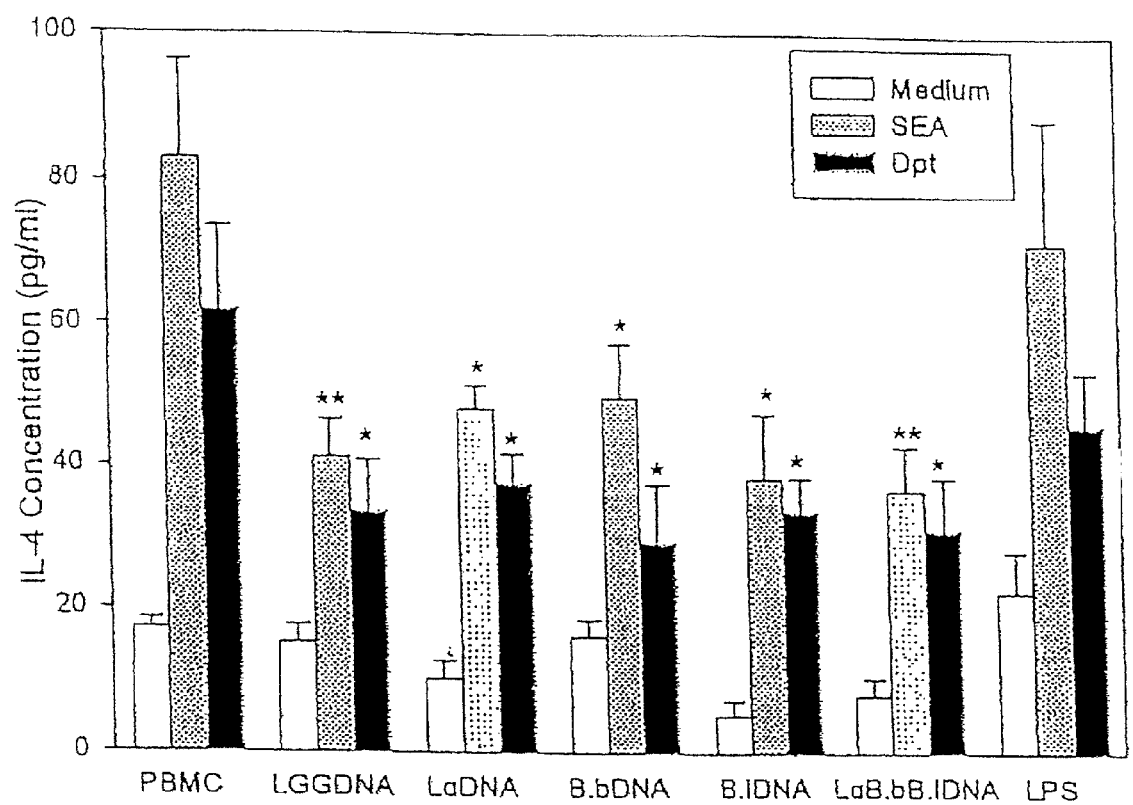
Figure 3:
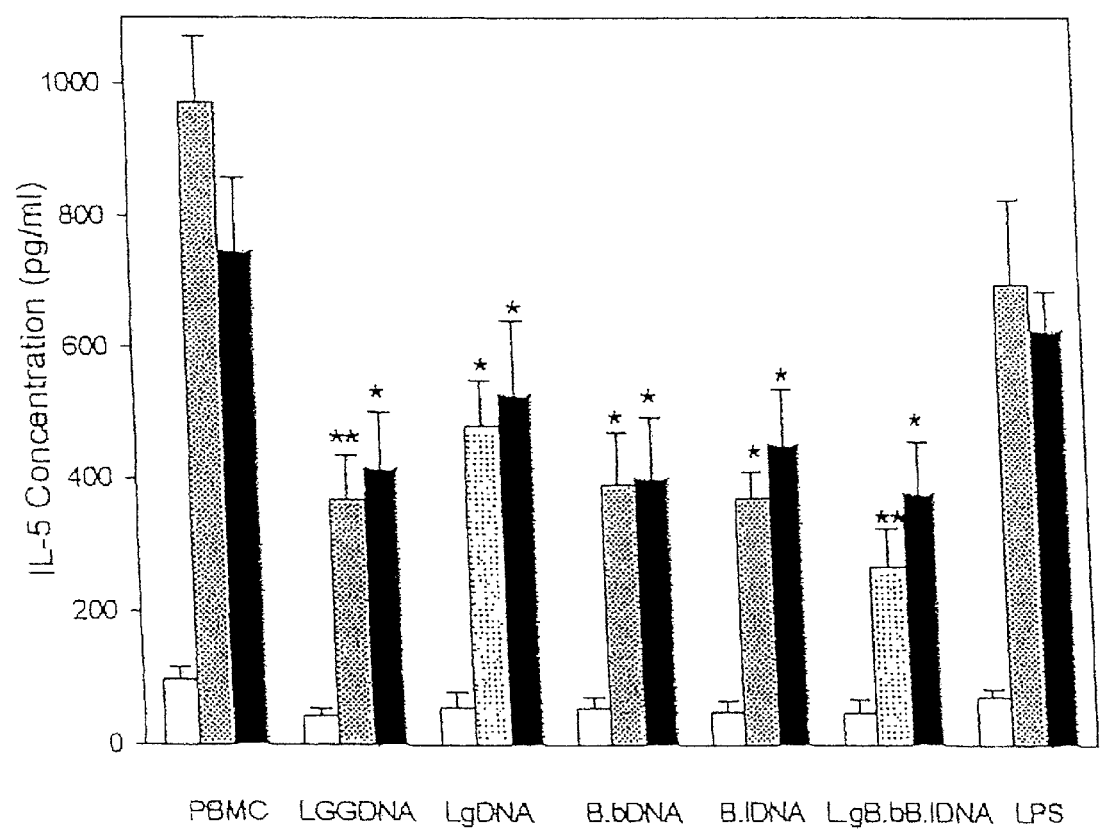
Figure 3:
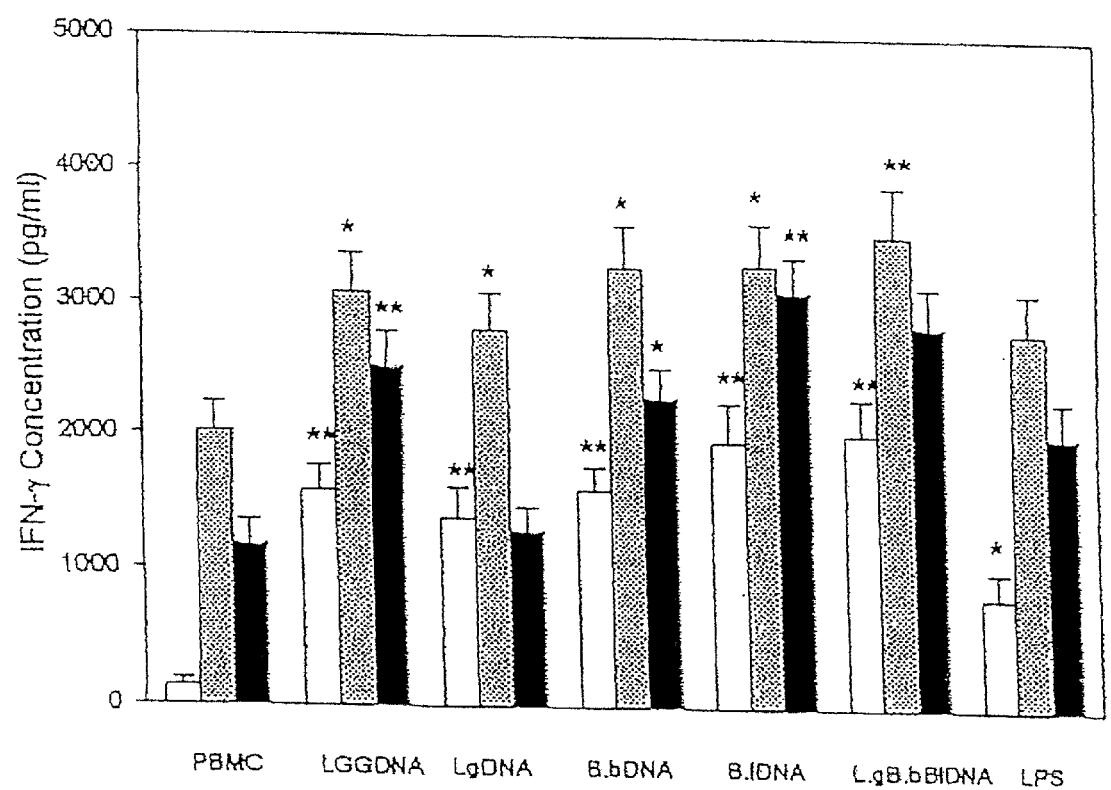
Figure 3:
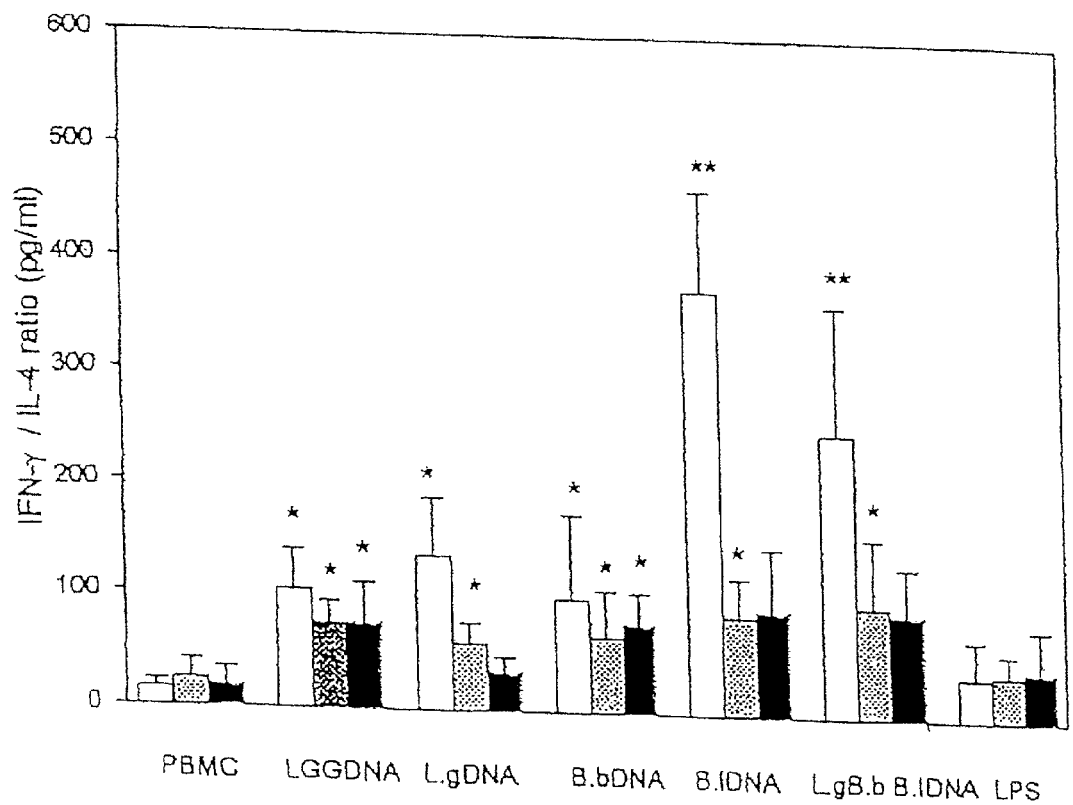

Furthermore, the inhibiting effect of genomic DNA from L. gasseri, B.b.B.l and LgsBbBl on IL-5 production from Dpt-stimulated PBMC from healthy test subjects was greater than in the case of allergic test subjects. But the growth-inhibiting effect of L. GG DNA on IL-5 production in healthy test subjects was the same as for allergic test subjects (FIG. 3). Consequently the genomic DNA from L. GG can modulate IL-5 production of Dpt-stimulated PBMC from healthy and allergic test subjects in the same manner.

Discussion

Allergies are hypersensitive reactions by the immune system to particular substances, called allergens (such as pollen, insects, poison, pharmaceuticals or food). Some experimental studies show that the allergic diseases can be linked to a disturbance of the $T_H1/T_H2$ cytokine balance with a relative preponderance of $T_H2$ cytokines and a lack of $T_H1$ cytokines. In fact, IL-4, IL-5, IL-3 and IL-9 are involved in triggering and maintaining allergic reactions. It was assumed that $T_H2$-type cytokines are preferentially involved in allergic diseases because the $T_H2$ to $T_H2$ immune response shift is very obvious in most type of allergic diseases. The encouraging results obtained in treating allergic patients with probiotic bacteria prompted us to elucidate the interaction between $T_H1/T_H2$ cytokines and allergies. Consequently, one strategy in the therapy of allergies is to change the $T_H1/T_H2$ balance by the administration of probiotic bacteria in order to restore the $T_H1/T_H2$ balance. Of particular interest are the results with respect to the capability of living or killed probiotic bacterial to significantly reduce the amount of IL-4 and increase the SFN-γ cytokine amounts. Furthermore, a current study proved that the protective effect of probiotic bacterial could be mediated by the release of soluble factors that change the permeability of the epithelium and protect against pathogenic bacterial invasions. These data raise the question of whether this soluble factor or other different cytoplasmic bacterial components, such as DNA, could be involved in triggering and modulation of cytokines. From this point of view, we researched the effect of living bacteria and pure genomic DNA from L. GG, L. gasseri, B. b, B.l strains and LgasBbBl (a mixture of L-gasseri B.b. and B.l) on the release of cytokines IL-4 and IL-5 using a human culture model. The results show that different strains of probiotic bacteria as well as their genomic DNA trigger significant changes in the profile of the cytokines that are actively secreted in vitro from SEA- or Dpt-stimulated PBMCs. Furthermore, they can modulate the $T_H1/T_H2$ balance by reducing the production of $T_H2$ cytokines and increase the production of $T_H1$ cytokines. Consequently such probiotic bacteria can exert a useful effect in allergic diseases as a result of their inhibiting effect on the production of $T_H2$ cytokines.

To investigate this effect, we first stimulated PBMC from healthy and allergic test subjects with SEA or Dpt (as a $T_H2$ cytokine-producing cell model). Numerous investigators reported that PBMCs secrete $T_H2$ cytokines after stimulation with superantigens. When, in this study, SEA or Dpt-stimulated PBMCs were preincubated with living probiotic bacteria and their genomic DNA, the production of $T_H2$ cytokines was reduced, but not in the presence of E. coli. In addition, this inhibiting effect was dependent on the dose, so that in a concentration of $2 \times 10^7$ CFU ml$^{-1}$ (corresponding to a ratio of 10:1 bacterial to PBMC), the inhibiting effect of living bacteria reached its maximum with respect to IL-4 and IL-5 production. Such a dosage-dependent effect is also reported in vitro for the production of IL-10 and IL-12 by monocytes from healthy test subjects after incubation with some strains of gram-positive bacteria. This study also showed that not only living probiotic bacteria, but also their genomic DNA can inhibit IL-4 and IL-5 production by SEA- or Dpt-stimulated PBMCs. The most important point of this study is that, firstly, it presents an advantageous effect of genomic DNA or probiotic bacteria on the cells of allergic patients that are sensitized to housedust mites; that is to say microscopic organisms that are found in homes. They are the prime cause of dust allergies.

Other reports are all only related to advantageous effects of living or killed probiotic bacteria on allergic diseases caused by food allergies or aeroallergens. Our data suggest that probiotic bacteria and their genomic DNA act by direct or indirect regulation of the signal path that is required for suppression of $T_H2$ cytokines, because the inhibiting effect was even observed when the probiotic bacteria and their genomic DNA were added before or simultaneously (for genomic DNA) with SEA- or Dpt-stimulation. Some experimental studies indicate that the modulation of the production of IL-4 and IL-5 is a multifactor process and some cytokines, such as IFN-γ are described as possible regulators of IL-4 production. Furthermore, it is reported that IL-12 is an outstanding cytokine in triggering the production of IFN-γ by human PBMCs. In our study, probiotic bacteria and their genomic DNA are capable of increasing IL-12 production by PBMC (data not shown).

In this respect, bacterial DNA was added to the SEA-stimulated PBMC culture and, interestingly, this experiment showed a multifarious IL-4 and IL-5 cytokine production after stimulation with bacterial DNA and SEA treatment. Bacterial DNA from probiotic bacteria reduced the IL-5 secretion more greatly than that from IL-4. Our data indicate that genomic DNA from probiotic bacteria can act as inhibitors for the production of IL-4 and IL-5 by SEA- and Dpt-stimulated PBMC from healthy and allergic test subjects. Moreover, a current study reports that heat-killed probiotic bacteria reduce IL-4 and IL-5 production by SEA-stimulated PBMCs. Considering that the preparation process, the gastrointestinal tract and high temperatures (70° C.) influence the viability of the bacteria, the results of these studies show a possible inhibiting effect of genomic DANN that is released by heat-killed bacteria and is added to PBMC. Various articles describe the response of various cytokines on CPG motifs which are present in the bacterial DNA, such as genomic DNA from L. GG. It would be interesting to know whether the strain-specific release of cytokines, which was demonstrated in this study, relates to the genomic sequence and the CPG motifs of each strain.

As far as we know, this report is the first one that shows the immuno-modulating effects of genomic DNAs of probiotic bacteria from SEA- or Dpt-stimulated PBMCs from healthy and allergic test subjects. The observed differences in the speed and magnitude of the inhibition of IL-4 and IL-5 as a response to bacterial DNAs and SEA- or Dpt-stimulation are interesting information about the influence of living or killed probiotic bacteria and/or bacterial components on the immune response. The growing knowledge about probiotics is exciting, but in the near future it must be ascertained which probiotic DNA (individual strains or a combination) has the strongest effect on particular diseases. Well-organized random clinical trials are further required to define the role of genomic DNA from probiotic bacteria as preventive and therapeutic agents in future.

Other objects and features of the present invention will become apparent when considered in combination with the accompanying drawing figures which illustrate certain preferred embodiments of the present invention. It should, however, be noted that the accompanying drawing figures are intended to illustrate only certain embodiments of the claimed invention and are not intended as a means for defining the limits and scope of the invention.

DETAILED DESCRIPTION OF THE DRAWING FIGURES

Further details and features of the invention are explained in greater detail below with reference to examples with the results of series of experiments. However, they are not intended to limit the invention but only explain it. In schematic view,

FIG. 1

Cytokine modulation of PBMC without (medium) or with stimulation by SEA and Dpt.

FIG. 2

Dosage-dependent inhibiting effect of living probiotic bacteria on the production of IL-4 (A), IL-5 (B) and (IFN-γ) by SEA stimulation of the PBMC of healthy test subjects.

FIG. 3

Growth-inhibiting effect of genomic DNA from probiotic bacteria on the production of IL-4, IL-5 and IFN-γ by SEA- or Dpt-stimulated PBMC from healthy (A, n=5) and allergic (B, n=5) test subjects.

FIG. 4

Dosage-dependent growth-inhibiting effect of genomic DNA on the production of IL-4 (A), IL-5 (B) and IFN-γ (C) by PBMC from healthy test subjects.

In detail, the figures show:

FIG. 1

Cytokine modulation of PBMC without (medium) or with stimulation by SEA and Dpt.

PBMCs from healthy (A, n=8) and allergic (B, n=8) test subjects were preincubated for 3 hours (at $2 \times 10^6$ cells/ml) with medium without (PBMC) or with four strains of probiotic bacteria, LgB.b.B.l (a mixture of probiotic bacteria and a gram-negative control bacterium (*E-coli* TG1) at a bacteria-to-cell ratio of 10:1 before either stimulation with the SEA-superantigen (2 μg ml$^{-1}$), Dpt (2 μg ml$^{-1}$) or not.

IL-4, IL-5 and IFN-γ were quantified after hours of incubation in supernatants by a specific ELISA study. The asterisks indicate particular suppression or stimulation ($*p<0.05$, $**p<0.01$) of $TH_2$ and $TH_1$ cytokine production compared to the control.

FIG. 2

Dosage-dependent inhibiting effect of living probiotic bacteria on the production of IL-4 (A), IL-5 (B) and (IFN-γ) by SEA stimulation of the PBMC of healthy test subjects. PBMC from four healthy donors ($2 \times 10^6$ cells ml$^{-1}$) was cultivated with four strains of probiotic bacteria, L. GG, *L. gasseri*, B.b., B.l. in concentrations of $5 \times 10^4$, $5 \times 10^5$, $2 \times 10^6$, $5 \times 10^6$, $2 \times 10^7$, $5 \times 10^7$ corresponding to 0.025, 0.25, 1, 2.5, 5, 10 and 25 bacteria-to-cell ratios for 3 hours before stimulation with 2 μg ml$^{-1}$ of SEA. After 48 hours' incubation, IL-4, IL-5 and IFN-γ were measured by specific ELISA. The error bar shows the standard errors of the mean.

FIG. 3

Growth-inhibiting effect of genomic DNA from probiotic bacteria on the production of IL-4, IL-5 and IFN-γ by SEA- or Dpt-stimulated PBMC from healthy (A, n=5) and allergic (B, n=5) test subjects. PBMC from five healthy and five allergic test subjects was incubated for 48 hours (at $2 \times 10^6$ cells ml$^{-1}$) with genomic DNA from 4 strains of probiotic bacteria, L. GG, *L. gasseri*, B.b., B.l. and LgBbBl (a mixture of *L. gasseri*, B.b and B.1.). At a concentration of 75 μg ml$^{-1}$ before stimulation with SEA (2 μg ml$^{-1}$) or Dpt (2000 SQ-EML$^{-1}$ corresponding to a 2 μg administration ml$^{-1}$). The medium and LPS (100 ng ml$^{-1}$) were used as control. IL-4, IL-5 and IFN-γ were quantified after 24 hours' incubation in supernatants by a specific ELISA study. The asterisks indicate outstanding inhibition ($*p<0.05$, $**p<0.01$) of cytokine production in comparison to the control (medium). The data are expressed as the mean+/−SEM:

FIG. 4

Dosage-dependent growth-inhibiting effect of genomic DNA on the production of IL-4 (A), IL-5 (B) and IFN-γ (C) by PBMC from healthy test subjects.

PBMC from 4 healthy donors was cultivated with various concentrations (5-105 mg ml$^{-1}$) of bacterial genomic DNA. The production of IL-4 (A) and IL-5 (B) was measured after 24 hours' incubation. The data are expressed as the mean+/−SEM.

While only several embodiments of the present invention have been shown and described, it will be obvious to those skilled in the art that many modifications may be made to the present invention without departing from the spirit and scope thereof.

What is claimed is:

1. A method for shifting the TH1-TH2 balance in a human body toward an increase of TH1 or a decrease of TH2 or both an increase in TH1 and a decrease in TH2 for treating persons suffering from allergic rhinitis, comprising the steps of:

preparing a pharmaceutical composition comprising:
viable or inactivated bacteria comprising genomic DNA of at least one probiotic, gram-positive bacteria strain selected from the group consisting of *Lactobacillus gasseri* PA 16/8, *Bifidobacterium bifidum* MF 20/5, *Bifidumbacterium longum* SP and a combination thereof,
as an active ingredient in said pharmaceutical composition being combined with an ingestible composition for forming an ingestible product, said genomic DNA of at least one probiotic, gram-positive bacteria strain being present in the form of at least one of viable bacteria and inactivated bacteria; and,
administering said genomic DNA as said viable or inactivated bacteria as part of said ingestible product to a human.

2. A method for shifting the TH1-TH2 balance in a human body toward an increase of TH1 or a decrease of TH2 or both an increase in TH1 and a decrease in TH2 for treating persons suffering from allergic rhinitis, comprising the steps of:

preparing a pharmaceutical composition comprising:
viable or inactivated bacteria comprising genomic DNA of at least one probiotic, gram-positive bacteria strain selected from the group consisting of *Lactobacillus gasseri* PA 16/8, *Bifidobacterium bifidum* MF 20/5, *Bifidumbacterium longum* SP 07/3 and a combination thereof,
as an active ingredient with said pharmaceutical composition being combined with a food supplement composition for forming a food product, said genomic DNA of at least one probiotic, gram-positive bacteria strain being present in the form of at least one of viable bacteria and inactivated bacteria; and,
orally administering said genomic DNA as said viable or inactivated bacteria as part of said food product to a human.

* * * * *